United States Patent
Ryu et al.

(10) Patent No.: US 11,083,798 B2
(45) Date of Patent: Aug. 10, 2021

(54) CONJUGATE INCLUDING PEPTIDE MOLECULE CAPABLE OF SELF-ASSEMBLY IN CELL ORGANELLE AND PHARMACEUTICAL COMPOSITION FOR PREVENTING OR TREATING CANCER INCLUDING CONJUGATE

(71) Applicant: UNIST (ULSAN NATIONAL INSTITUTE OF SCIENCE AND TECHNOLOGY), Ulsan (KR)

(72) Inventors: Ja Hyoung Ryu, Ulsan (KR); Manayath Thekkeyil Jeena, Ulsan (KR)

(73) Assignee: Unist (Ulsan National Institute of Science and Technology), Ulsan (KR)

( * ) Notice: Subject to any disclaimer, the term of this patent is extended or adjusted under 35 U.S.C. 154(b) by 283 days.

(21) Appl. No.: 15/813,646

(22) Filed: Nov. 15, 2017

(65) Prior Publication Data
US 2018/0133330 A1      May 17, 2018

(30) Foreign Application Priority Data
Nov. 16, 2016   (KR) .................. 10-2016-0152392

(51) Int. Cl.
| | |
|---|---|
| *A61K 47/54* | (2017.01) |
| *C07K 5/087* | (2006.01) |
| *A61P 35/00* | (2006.01) |
| *A61K 38/00* | (2006.01) |

(52) U.S. Cl.
CPC ............ *A61K 47/548* (2017.08); *A61K 47/54* (2017.08); *A61P 35/00* (2018.01); *C07K 5/0812* (2013.01); *A61K 38/00* (2013.01)

(58) Field of Classification Search
CPC ...... A61K 38/00; A61K 47/54; A61K 47/548; A61P 35/00; C07K 5/0812
See application file for complete search history.

(56) References Cited

PUBLICATIONS

Janet Plescia, Rational design of shepherdin, a novel anticancer agent, Cancer Cell : May 2005 ■ vol. 7, pp. 457-468.*
Huaimin Wang, Integrating Enzymatic Self-Assembly and Mitochondria Targeting for Selectively Killing Cancer Cells without Acquired Drug Resistance, J. Am. Chem. Soc. Nov. 14, 2016, 138, 16046-16055.*
Catherine K. Smith, Construction and Design of â-Sheets, Acc. Chem. Res. 1997, 30, 153-161.*
Abu-Gosh et al., "Multiple Triphenylphosphonium Cations Shuttle a Hydrophilic Peptide into Mitochondria," *Molecular Pharmaceutics*. 6 (1138-1144) Jun. 17, 2009.
Marchesan et al., "The Phe-Phe Motif for Peptide Self-Assembly in Nanomedicine," *Molecules*. 20 (19775-19788) Nov. 3, 2015.
Korean Intellectual Property Office, Office action, dated Sep. 7, 2018, issued in Republic of Korea Patent Application No. 10-2016-0152392.

* cited by examiner

*Primary Examiner* — James H Alstrum-Acevedo
*Assistant Examiner* — Erinne R Dabkowski
(74) *Attorney, Agent, or Firm* — Klarquist Sparkman, LLP

(57) ABSTRACT

Disclosed are a conjugate including a mitochondria-targeting moiety and a peptide molecule capable of self-assembly; and a pharmaceutical composition for preventing or treating cancer including the conjugate as an active ingredient.

12 Claims, 27 Drawing Sheets

Intra-mitochondrial fibril formation of Mito-FF

Mito-GG treated

Mito-VV, R = Val
Mito-FxFx, R = Cha
Mito-GG, R = Gly

CONJUGATE INCLUDING PEPTIDE MOLECULE CAPABLE OF SELF-ASSEMBLY IN CELL ORGANELLE AND PHARMACEUTICAL COMPOSITION FOR PREVENTING OR TREATING CANCER INCLUDING CONJUGATE

CROSS-REFERENCE TO RELATED APPLICATION

This application claims priority to and the benefit of Korean Patent Application No. 10-2016-0152392, filed on Nov. 16, 2016, in the Korean Intellectual Property Office, the disclosure of which is incorporated by reference herein in its entirety.

BACKGROUND

1. Field

One or more embodiments relate to a conjugate including a mitochondria-targeting moiety and a peptide molecule capable of self-assembly; and a pharmaceutical composition for preventing or treating cancer including the conjugate as an active ingredient.

2. Description of the Related Art

Molecular self-assembly is one of the most attractive strategies for creating functional nanomaterials which have integral biomedical applications to drug delivery, tissue engineering, and gene therapy, etc. Even though nanostructural assembly has been investigated extensively in a bulk solvent, intracellular assembly of synthetic peptide amphiphiles has not yet been studied deeply, and is one of the emerging topics of research regarding biomimetic assembly for regulation of cellular functions.

Mitochondria are highly dynamic cellular organelles which produce energy via oxidative phosphorylation, and not only have a crucial role in cellular functions such as fatty acid oxidation, the tricarboxylic acid (TCA) cycle, and amino acid metabolism, but are also involved in major pathways of cell death mechanisms such as apoptosis, necrosis, and necroptosis. Abnormalities in mitochondrial function have been documented in several neurodegenerative diseases associated with accumulation of protein fibrils in the brain, including Alzheimer's disease, Parkinson's disease, Huntington's disease, and amyotrophic lateral sclerosis. Accumulations of abnormally folded proteins rich in beta-sheet conformations, such as Aβ, have been observed in mitochondria of patients suffering from Alzheimer's disease. These abnormally folded proteins are known to have cytotoxic effects.

SUMMARY

One or more embodiments include a conjugate including a mitochondria-targeting moiety, an intracellular component, e.g., a peptide molecule capable of self-assembly in mitochondria, and a fluorophore, or pharmaceutically acceptable salt of the conjugate.

The conjugate includes a mitochondria-targeting moiety and a peptide represented by $(Xaa)_n$-Lys, the mitochondria-targeting moiety being bound to a lysine amino acid of the peptide. Xaa represents an amino acid and n indicates the number of Xaa bound via a peptide bond, wherein n is an integer in a range of about 2 to about 200, about 2 to about 150, about 2 to about 100, about 2 to about 50, about 2 to about 40, about 2 to about 30, about 2 to about 20, about 2 to about 15, about 2 to about 10, about 2 to about 8, about 2 to about 6, about 2 to about 4, or about 2 to about 3, and Xaa is selected from the group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine, tryptophan, and a variant bound to a $C_3$-$C_{10}$ cycloalkyl group, but embodiments are not limited thereto.

In addition, a beta-sheet secondary structure is formed between at least two amino acids, and the peptide includes the beta-sheet secondary structure, but embodiments are not limited thereto.

One or more embodiments include a pharmaceutical composition for preventing or treating cancer including the conjugate or a pharmaceutically acceptable salt thereof as an active ingredient.

One or more embodiments include a method of preventing or treating cancer including: administering the conjugate or a pharmaceutically acceptable salt thereof to a subject that needs the conjugate or a pharmaceutically acceptable salt thereof.

Additional aspects will be set forth in part in the description which follows and, in part, will be apparent from the description, or may be learned by practice of the presented embodiments.

The present inventors identified whether fibrous self-assembly in mitochondria of carcinoma cells induces cytotoxicity so as to remove the carcinoma cells. Thereby the present invention was achieved.

Besides offering applications as biomaterials, fibrous assembly of synthetic materials inside cells may serve as an innovative approach to alter cellular functions via interactions thereof with cell components which eventually leads to exploration of undefined mechanisms inside the cells. Formation of similar fibrils or oligomers thereof has been reported in several neurodegenerative diseases which cause loss of integrity of membrane-bound organelles, such as lysosomes or mitochondria, and consequently induce toxicity.

Inspired by this observation, a technology was developed in the present invention, the technology being of inducing programmed cell death as a result of loss of membrane integrity due to self-assembly of synthetic peptides inside mitochondria of carcinoma cells.

In order to prove this concept, Mito-FF was designed in the present invention, Mito-FF being a mitochondria-targeting conjugate and equipped with triphenylphosphonium (TPP) as a targeting ligand, dipeptide of phenylalanine (FF) as a fiber-forming building block, and pyrene as a fluorophore for fluorogenic detection of fibril formation inside a mitochondrion. A fluorescence emission image of pyrene as well as an electron micrograph confirms mitochondrial assembly of Mito-FF.

A self-assembly process is accelerated by a high mitochondrial accumulation of peptides, which is driven by a negative inner membrane potential of carcinoma cell mitochondria. In the present invention, Mito-FF is innocuous towards normal cell lines on account of reduced negative membrane potential which results in no fibril formation inside mitochondria.

In one or more embodiments of the present invention, a conjugate may include a mitochondria-targeting moiety and a peptide represented by $(Xaa)_n$-Lys, the mitochondria-targeting moiety being bound to the lysine (Lys), wherein Xaa represents an amino acid, n indicates the number of Xaa bound via a peptide bond, n may be an integer from about 2 to about 200, Xaa may be selected from the group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine, tryptophan, and a variant bound to a $C_3$-$C_{10}$ cycloalkyl group, the amino acid may form a beta-sheet secondary structure between at least two amino acids, and the peptide may include the beta-sheet secondary structure.

The term "peptide" as used herein refers to chains of 3 to 201 amino acid monomers linked by peptide bonds. The peptide may be represented by $(Xaa)_n$-Lys. n indicates the number of amino acids bound via a peptide bond, and may be an integer in a range of about 2 to about 200, about 2 to about 150, about 2 to about 100, about 2 to about 50, about 2 to about 40, about 2 to about 30, about 2 to about 20, about 2 to about 15, about 2 to about 10, about 2 to about 8, about 2 to about 6, about 2 to about 4, or about 2 to about 3, and Xaa may be selected from the group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine, tryptophan, and a variant bound to a $C_3$-$C_{10}$ cycloalkyl group. For example, n may be 2, and the two Xaa may both be phenylalanine, alanine, cyclohexylalanine, or valine, bound to each other via a peptide bond, but embodiments are not limited thereto.

The peptide represented by $(Xaa)_n$-Lys may be a peptide of variants connected to each other via a peptide bond in which a $C_3$-$C_{10}$ cycloalkyl group is a bound to each amino acid or an R group thereof, from an N-terminus to a C-terminus thereof (a variant bound to a $C_3$-$C_{10}$ cycloalkyl group), but embodiments are not limited thereto.

A hydroxy group of a C-terminus carboxyl group of lysine in the peptide represented by $(Xaa)_n$-Lys may be substituted with a group selected from the group consisting of an amine group, an alkyl group, an alcohol group, a ketone group, an acyl group, an ester group, an ether group, an acetyl group, an acyl halide group, and an aldehyde group; a specific chemical group may not be bound to a position of the hydroxy group; or a different chemical group may be bound thereto via a chemical bond, for example, an amine group may be bound thereto.

The term "variant bound to a $C_3$-$C_{10}$ cycloalkyl group", as used herein, may refer to a variant in which carbon of an R group is bound to a $C_3$-$C_{10}$ cycloalkyl group. For example, the variant bound to a $C_3$-$C_{10}$ cycloalkyl group may be cyclohexylalanine (CHA) in which carbon of an R group of alanine, i.e., a methyl group, is bound to a cyclohexyl group, but embodiments are not limited thereto.

The peptide may include a beta-sheet secondary structure, and the peptide may form the beta-sheet secondary structure inside the peptide or between at least two amino acids of another peptide, but embodiments are not limited thereto.

The beta-sheet secondary structure is one of secondary structures formed by interactions of amino acid sequences constituting protein, and is formed by hydrogen bonds between stable molecules that are horizontally connected. The beta-sheet secondary structure is known as being relevant to protein aggregates or fibril formation in a number of human diseases.

The term "mitochondria-targeting moiety" as used herein refers to a moiety having a function of targeting a specific material into mitochondria inside a cell. For example, the mitochondria-targeting moiety may be triphenylphosphonium (TPP), but embodiments are not limited thereto.

In addition, due to the mitochondria-targeting moiety included in the conjugate, according to the present invention, the conjugate may be targeted to mitochondria inside a cell. Thus, the conjugate may pass through double membranes of the mitochondria so that the conjugate may enter inside the mitochondria.

In the present invention, the conjugate may enter mitochondria due to the mitochondria-targeting moiety. The conjugate that has entered the mitochondria may carcinoma cell-specifically induce self-assembly of peptides synthesized inside the mitochondria of carcinoma cells, thereby inducing apoptosis thereof.

Regarding the self-assembly in mitochondria of carcinoma cells, in carcinoma cells, accumulation of peptides included in the pharmaceutical composition may be driven by highly negative inner membrane potential of mitochondria of the carcinoma cells such that a self-assembly process is accelerated. However, in normal cells, the negative inner membrane potential may be low, as compared with carcinoma cells, and thus accumulation of peptides may not be sufficient, and fibril formation driven by self-assembly inside mitochondria may not occur, which may not result in the induction of self-assembly.

The number of the mitochondria-targeting moiety bound to the peptide may be an integer in a range of 1 to the number of amine groups present in the peptide represented by $(Xaa)_n$-Lys. In a case where an amine group is present at a C-terminus of the peptide, the number of the mitochondria-targeting moiety bound to the peptide may be an integer from about 1 to m+1 (the number of lysine amino acids (m) plus 1). In some embodiments, the number of the mitochondria-targeting moiety bound to the peptide may be 1 or 2, but embodiments are not limited thereto.

In the present invention, an N-terminus of the peptide of the conjugate may be bound to a fluorophore via an amide bond, but embodiments are not limited thereto.

The term "fluorophore" refers to an atomic group necessary for fluorescence of organic compounds. In the present invention, the fluorophore may be bound to an N-terminus of the peptide via an amide bond and may be at least one selected from the group consisting of pyrene, 4-nitro-2,1,3-benzoxadiazole (NBD), perylene, naphthalene, coronene, and a fluorophore including aromatic compounds having a planar structure in which the aromatic compounds may be likely to be stacked upon one another through pi bonding, but embodiments are not limited thereto.

The peptide and the mitochondria-targeting moiety; the peptide and the fluorophore; or the peptide, the mitochondria-targeting moiety, and the fluorophore may be connected directly or via a linker. The linker may be selected from a $C_1$-$C_{10}$ alkyl group, a $C_1$-$C_5$ alkyl group, a $C_1$-$C_4$ alkyl group, a $C_2$-$C_3$ alkyl group, a $C_1$-$C_{10}$ alkene group, a $C_1$-$C_5$ alkene group, a $C_1$-$C_4$ alkene group, a $C_2$-$C_3$ alkene group, a $C_1$-$C_{10}$ alkyne group, a $C_1$-$C_5$ alkyne group, a $C_1$-$C_4$ alkyne group, and a $C_2$-$C_3$ alkyne group, but embodiments are not limited thereto. In addition, the linker may include at a terminal a functional group that may form a suitable bond, e.g., an amide bond, to a peptide.

The conjugate or pharmaceutically acceptable salt thereof may be represented by Formula 1:

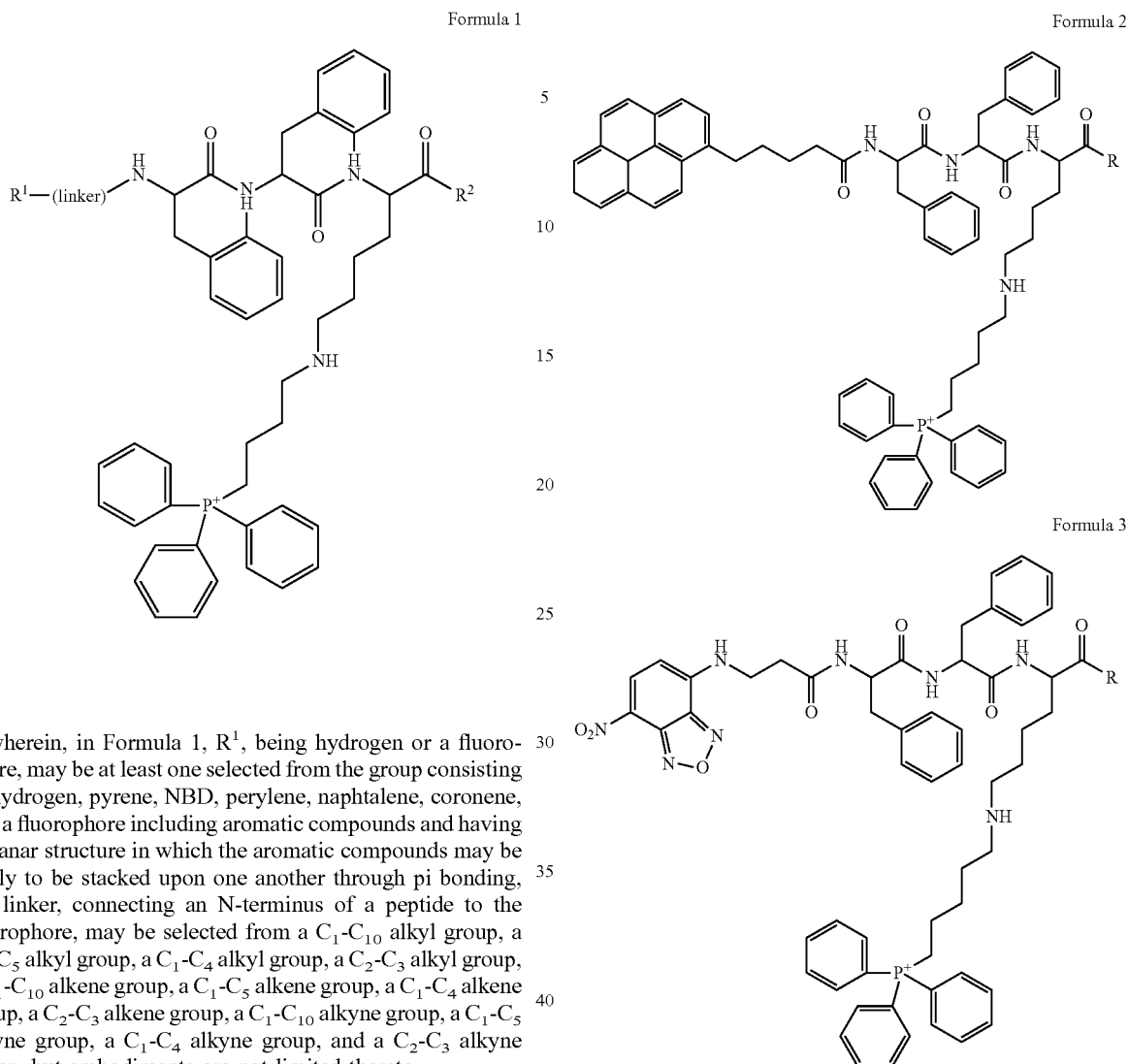

Formula 1

Formula 2

Formula 3 wherein, in Formula 1, $R^1$, being hydrogen or a fluorophore, may be at least one selected from the group consisting of hydrogen, pyrene, NBD, perylene, naphtalene, coronene, and a fluorophore including aromatic compounds and having a planar structure in which the aromatic compounds may be likely to be stacked upon one another through pi bonding, the linker, connecting an N-terminus of a peptide to the fluorophore, may be selected from a $C_1$-$C_{10}$ alkyl group, a $C_1$-$C_5$ alkyl group, a $C_1$-$C_4$ alkyl group, a $C_2$-$C_3$ alkyl group, a $C_1$-$C_{10}$ alkene group, a $C_1$-$C_5$ alkene group, a $C_1$-$C_4$ alkene group, a $C_2$-$C_3$ alkene group, a $C_1$-$C_{10}$ alkyne group, a $C_1$-$C_5$ alkyne group, a $C_1$-$C_4$ alkyne group, and a $C_2$-$C_3$ alkyne group, but embodiments are not limited thereto.

In addition, the linker may include at a terminal a functional group that may form a suitable bond, e.g., an amide bond, to the peptide, and may connect the peptide, via an amide bond, to at least one selected from the group consisting of pyrene, NBD, perylene, naphtalene, coronene, and a fluorophore including aromatic compounds and having a planar structure in which the aromatic compounds may be likely to be stacked upon one another through pi bonding.

In a case where $R^1$ is hydrogen, a linker may not be present, and $R^2$ may be a C-terminus of the peptide (i.e., a C-terminus of lysine), and may be at least one selected from the group consisting of a hydroxy group (—OH), an amine group, an alkyl group, an alcohol group, a ketone group, an acyl group, an ester group, an ether group, an acetyl group, an acyl halide group, and an aldehyde group, wherein the alkyl group, the alcohol group, the ketone group, the acyl group, the ester group, the ether group, the acetyl group, and the acyl halide group may each independently have carbon atoms in a range of 1 to 20, 1 to 10, or 1 to 5.

In one or more embodiments, the conjugate or pharmaceutically acceptable salt thereof may be represented by Formula 2 or Formula 3, but embodiments are not limited thereto:

When R is an amine group in Formula 2, the conjugate is referred to as Mito-FF described in Examples. Mito-FF may self-assemble in mitochondria of carcinoma cells with the same or different conjugate to form fibrils. When R is an amine group in Formula 3, the conjugate is referred to as Mito-FF-NBD described in Examples. Mito-FF-NBD may self-assemble in mitochondria of carcinoma cells with the same or different conjugate to form fibrils.

In the present invention, the conjugate may be amphiphilic. The term "amphiphilic" as used herein refers to a state of having affinity for both polar and nonpolar materials. In the conjugate according to the present invention, a nonpolar amino acid in a peptide and a fluorophore may be hydrophobic, and a polar amino acid may be hydrophilic, and thus the conjugate may be amphiphilic as a whole, but embodiments are not limited thereto.

The conjugate may be in form of isomer. The term "isomer" as used herein refers to a compound with the same molecular formula as another molecule, but with a different spatial positioning. The isomer may refer to a stereoisomer. The stereoisomer include enantiomers and diastereomers. An enantiomer, also known as an optical isomer, is one of two stereoisomers that are mirror images of each other that are non-superposable, as one's left and right hands. Diastereomers are stereoisomers that are not mirror images of each other. Diastereomers include isomers having different spatial arrange of constituting atoms and cis-trans isomers having different spatial arrange of atoms due to restricted rotation around a carbon-carbon bond in alkenes and cycloalkanes.

In one or more embodiments of the present invention, a pharmaceutical composition for preventing or treating cancer may include a conjugate or a pharmaceutically acceptable salt thereof, wherein the conjugate may include a mitochondria-targeting moiety and a peptide represented by $(Xaa)_n$-Lys, the mitochondria-targeting moiety may be bound to the lysine (Lys), Xaa represents an amino acid, n indicates the number of Xaa bound via a peptide bond, n may be an integer from about 2 to about 200, Xaa may be selected from the group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine, tryptophan, and a variant bound to a $C_3$-$C_{10}$ cycloalkyl group, a beta-sheet secondary structure may be formed between at least two amino acids, and the peptide may include the beta-sheet secondary structure.

The conjugate may be present as a pharmaceutically acceptable salt. The pharmaceutically acceptable salt may include an acid addition salt or a base addition salt and stereoisomers thereof. For example, the pharmaceutically acceptable salt may be an addition salt of an organic acid or an addition salt of an inorganic acid. The pharmaceutically acceptable salt is not particularly limited as long as it contains any salt that maintains activity of a parent compound in a subject to be administered and does not cause any undesirable effect.

The pharmaceutically acceptable salt may include inorganic and organic salts. For example, the pharmaceutically acceptable salt may be acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, lactic acid, bicarboxylic acid, unsulfuric acid, bitartaric acid, oxalic acid, butylic acid, edetate calcium, carbonic acid, chlorobenzoic acid, citric acid, edetic acid, toluenesulfonic acid, fumaric acid, gluceptic acid, ethylic acid, pamoic acid, gluconic acid, methylnitric acid, malonic acid, hydrochloric acid, hydroiodic acid, hydroxynaphthoic acid, isethionic acid, lactobionic acid, mandelic acid, mucic acid, nafcillin acid, muconic acid, p-nitromethanesulfonic acid, hexamic acid, pantothenic acid, monohydrogenphosphoric acid, dihydrogenphosphoric acid, salicylic acid, sulfamic acid, sulfanilic acid, or methanesulfonic acid.

In addition, the pharmaceutically acceptable salt may be in form of an alkali and alkaline earth metal salt, e.g., ammonium salt, lithium salt, sodium salt, potassium salt, magnesium salt, and calcium salt; a salt having an organic base, e.g., benzathine, N-methyl-D-glucamine, and hydrabamine salt; and a salt having an amino acid such as arginine or lysine. The salt form may also be converted to a free form by treatment with a suitable base or acid.

A pharmaceutical composition for preventing or treating cancer including the conjugate or a pharmaceutically acceptable salt thereof as an active ingredient may induce apoptosis by self-assembly in mitochondria of carcinoma cells.

The apoptosis is a form of cell death regulated by genes, and is distinguished from necrosis, which is cell death caused by local death or pathological death of cells, e.g., by burns, bruise, poisons, etc. The apoptosis refers to cell death when a cell starts to shrink, a gap is created between adjacent cells, and DNA is regularly cleaved and fragmented in the cell.

The pharmaceutical composition may be used in prevention or treatment of solid cancer or haematological cancer; or primary cancer or metastatic cancer. For example, the cancer may be selected from the group consisting of cervical cancer, liver cancer, skin cancer, prostate cancer, breast cancer, mammary cancer, nasopharynx adenocarcinoma, lung cancer, or brain tumor, but embodiments are not limited thereto.

The pharmaceutical composition of the present invention may be in any suitable form for an intended mode of administration. Regarding the pharmaceutical composition of the present invention, the term "administration" as used herein refers to introducing a given substance into a patient by any suitable method. An administration route of the pharmaceutical composition may be any suitable general route as long as a drug may reach a target tissue. For example, the administration may be intraperitoneal administration, intravenous administration, intramuscular administration, subcutaneous administration, intravenous administration, oral administration, topical administration, intranasal administration, intrapulmonary administration, or rectal administration, but embodiments are not limited thereto. The pharmaceutical composition of the present invention may be administered by any suitable device capable of transferring an active ingredient to a target cell.

The pharmaceutical composition of the present invention may be orally or parenterally administered. The pharmaceutical composition may be orally administered. When the pharmaceutical composition of the present invention is parenterally administered, the pharmaceutical composition may be administered by intravenous injection, subcutaneous injection, muscle injection, and intraperitoneal injection, or the like. Regarding the pharmaceutical composition of the present invention, the administration route thereof may be determined depending on a type of disease to which the pharmaceutical composition is applied.

In one embodiment, a pharmaceutical composition for preventing or treating cancer may be formulated in an oral dosage form or in a parenteral dosage form.

The pharmaceutical composition of the present invention may be prepared, by a suitable known method, in an oral dosage form, e.g., powders, granules, tablets, capsules, suspensions, emulsions, syrups, aerosols and the like; or in a parenteral dosage form, e.g., suspensions, emulsions, freeze-dried preparations, external preparations, suppositories, sterilized injection solutions, preparations for transplantation.

The pharmaceutical composition may further include a pharmaceutically acceptable excipient that may be used for formulation, in addition to an active ingredient (i.e., conjugate or a pharmaceutically acceptable salt thereof).

The pharmaceutically acceptable excipient that may be used for formulation of the pharmaceutical composition may be at least one selected from the group consisting of a carrier, a vehicle, a diluent, a solvent, e.g., primary alcohol, e.g., ethanol, isopropanol, and polyhydric alcohol, e.g., glycerol and edible oil, e.g., soybean oil, coconut oil, olive oil, safflower oil, and cottonseed oil, oily esters, e.g., ethyl oleate and isopropyl myristate, a bonding agent, an adjuvant, a solubilizer, a thickener, a stablizer, a disintegrant, a glident, a lubricant, a buffer, an emulsifier, a humectant, a suspension, a sweetener, a colorant, a flavoring agent, a coating agent, a preservative, an antioxidant, a processing agent, a drug delivery modifier, and an enhancer, e.g., calcium phosphate, magnesium stearate, talc, monosaccharide, disaccharide, starch, gelatin, cellulose, methylcellulose, sodium carboxymethylcellulose, dextrose, hydroxypropyl-β-cyclodextrin, polyvinylpyrrolidone, low melting point wax, and ion exchange resin, but embodiments are not limited thereto.

A pharmaceutically acceptable carrier included in the pharmaceutical composition may be any suitable carrier generally included in preparation. The pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but embodiments are not limited thereto. The pharmaceutical composition may further include, in addition to the foregoing ingredients, a lubricant, a humectant, a sweetener, a flavoring agent, an emulsifier, a suspension, or a presevative. The pharmaceutically acceptable carrier and preparation that are suitable for use are described in detail in Remington's Pharmaceutical Sciences (19th ed., 1995).

The pharmaceutical composition may be formulated in form of various oral dosage forms. For example, the pharmaceutical composition may be any suitable oral dosage form, such as tablets, pills, hard or soft capsules, liquids, suspensions, emulsions, syrups, granules, elixirs or the like. Such oral dosage forms may contain a pharmaceutically acceptable carrier in addition to an active ingredient according to the general configuration of each formulation. The pharmaceutically acceptable carrier may include a diluent, e.g., lactose, dextrose, sucrose, mannitol, sorbitol, cellulose and/or glycine; and a lubricant, e.g., silica, talc, stearic acid or its magnesium salt or calcium salt, and/or polyethylene glycol.

When the oral dosage form is in form of tablets, the oral dosage form may include a binder, e.g., magnesium aluminum silicate, starch paste, gelatin, tragacanth, methylcellulose, sodium carboxymethylcellulose and/or polyvinylpyrrolidine. If necessary, the oral dosage form may also include a disintegrant, e.g., starch, agar, alginic acid or its sodium salt, an azeotropic mixture, an absorbent, a coloring agent, a flavoring agent, a sweetening agent, and the like.

Moreover, the pharmaceutical composition may be formulated in form of parenteral dosage forms. Parenteral dosage forms include subcutaneous injection, intravenous injection, intramuscular or intrathoracic injection. To prepare a parenteral dosage form, an active ingredient of the pharmaceutical composition may be mixed with a stabilizer or a buffer in water to prepare a solution or suspension which may then be prepared in form of an ampule or vial for unit dosage.

The pharmaceutical composition may be sterilized or may further contain excipients, including preservatives, stabilizers, wettable powder or emulsifying agents, salts for control for osmotic pressure and/or buffers, and other therapeutically useful substances. The pharmaceutical composition may be formulated according to a general mixing, granulation, or coating method.

An amount of the conjugate or a pharmaceutically acceptable salt thereof in the pharmaceutical composition may be properly controlled according to the purpose of use or type of dosage forms. For example, the amount of the conjugate or a pharmaceutically acceptable salt thereof may be in a range of about 0.001 percent by weight (wt %) to about 99 wt %, about 0.001 wt % to about 90 wt %, about 0.001 wt % to about 50 wt %, about 0.01 wt % to about 50 wt %, about 0.1 wt % to about 50 wt %, or about 1 wt % to about 50 wt %, but embodiments are not limited thereto.

With regard to the conjugate or a pharmaceutically acceptable salt thereof in the pharmaceutical composition, a "therapeutically effective amount" refers to a sufficient amount which is therapeutically effective upon being administered to a subject in a need of treatment. The therapeutically effective amount may be determined according to the type of disease, severity of disease, type of administered active ingredient, type of formulation, patient's age, sex, weight, health conditions, diet, drug administration time, and administration method. For example, to mammals including humans, the therapeutically effective amount may be in a range of about 0.01 mg/kg to about 500 mg/kg (body weight). The therapeutically effective amount may differ depending on the desired effects, for example, effects of treatment and/or prevention on cancer. The therapeutically effective amount may be administered via an oral route or a parental route (e.g., intravenous injection or intramuscular injection) once a day or twice or more a day.

BRIEF DESCRIPTION OF THE DRAWINGS

The foregoing and other aspects will become apparent and more readily appreciated from the following description of the embodiments, taken in conjunction with the accompanying drawings in which.

DETAILED DESCRIPTION

Figure 1:
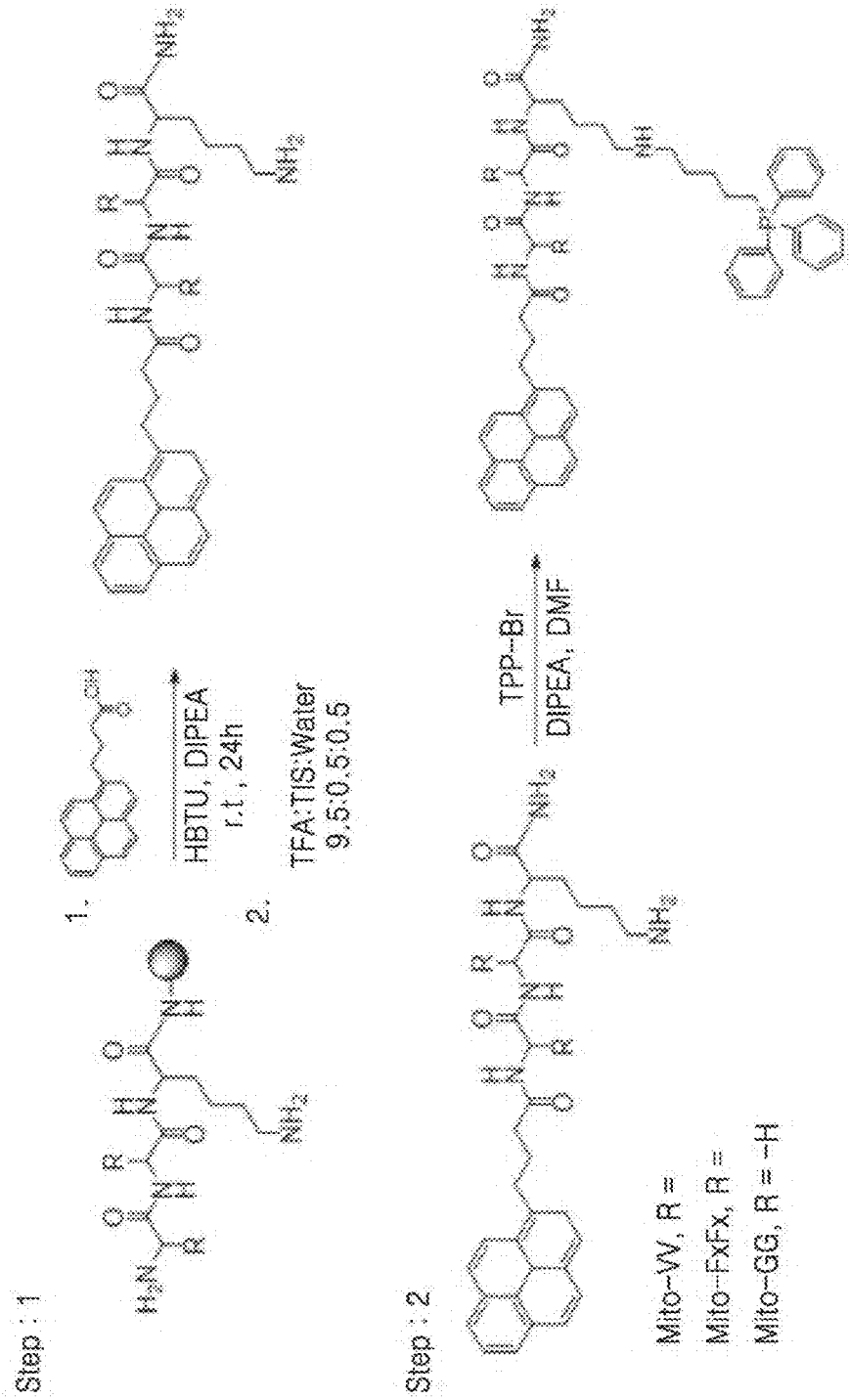
FIG. 1 is a reaction scheme that illustrates a process of synthesis of Mito-FF, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Hereinafter, the present invention will be described in further detail with reference to Examples. However, these Examples are for illustrative purposes only, and the present invention is not intended to be limited by these Examples.

Example 1. Synthesis and Characterization of Mito-FF

Mito-FF consists of a tripeptide building block Phe-Phe-Lys (FFK), synthesized based on 9-fluorenylmethoxycarbonyl chemistry (Fmoc) via the standard solid phase synthesis (SSPS) as follows.

The Mito-FF was synthesized by the standard 9-fluorenylmethoxycarbonyl solid-phase peptide synthesis on a 0.25 mmol scale. The synthesized peptide was treated with 1-pyrene carboxylic acid (500 μmol) and O-(Benzotriazol-1-yl)-N,N,N',N'-tetramethyluronium hexafluorophosphate (HBTU, 500 μmol) in presence of diisopropyl ethyl amine (DIPEA, 500 μmol) and allowed to stir at room temperature for 24 hours in dimethylformamide (DMF). A resin was collected by filtration and washed with DMF to remove unreacted chemicals. The product cleaved from the resin with cleavage cock tail TFA/water/tri isopropyl amine mixture (9.5:0.5:0.5) was precipitated in a cold condition. The resulting product was purified by high-performance liquid chromatography (HPLC) and confirmed by mass analysis using MALDI-TOF/TOF. To achieve the triphenyl phosphonium (TPP) conjugation, synthesized peptide (0.02 mmol) was treated with 1-hexyl triphenylphosphonium bromide salt (0.04 mmol) with tri ethyl amine (0.02 mmol) in DMF, and allowed to stir for 12 hours at room temperature. The pure product was purified using HPLC, freeze dried, and then stored.

FIG. 1 is a schematic representation for the foregoing synthesis process.

Figure 2:
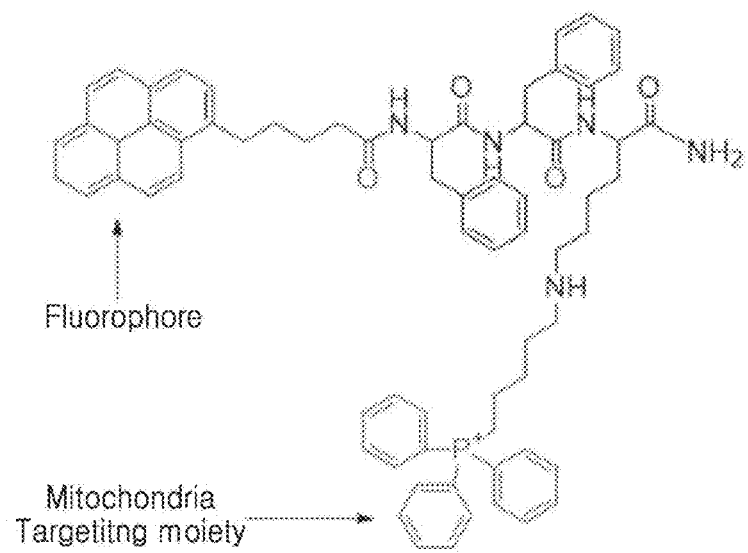
FIG. 2 is a schematic view that illustrates a molecular structure of Mito-FF, according to an embodiment.

As shown in FIG. 2, an N-terminus of the synthesized Mito-FF is conjugated with pyrene (butyric acid) to enable fluorescent detection, and an amine group of a side chain of lysine is conjugated with TPP for targeting mitochondria. The pyrene moiety in Mito-FF not only serves as a fluorophore but also increases the self-assembling propensity by enhancing the hydrophobicity and pi-pi interactions.

Figure 3:
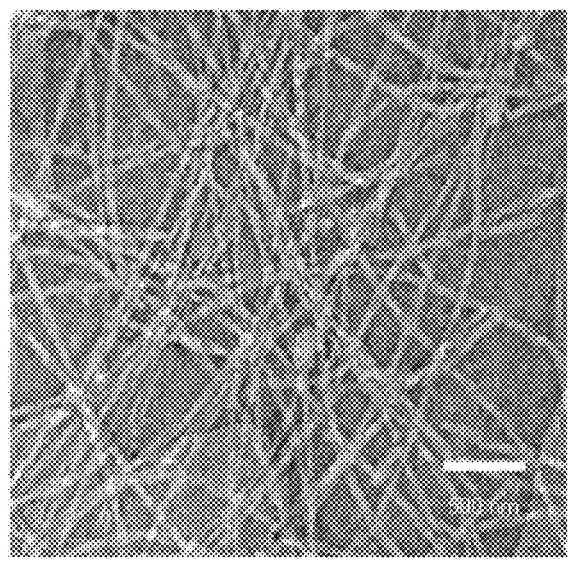
FIG. 3 is a transmission electron microscopy (TEM) image that shows Mito-FF present in water, according to an embodiment.

As shown in FIG. 3, it was found that Mito-FF was self-assembled into nanofibers with an average length of 500 nm and an average width of 10 nm for individual fibers, in both saline phosphate buffers (10 millimolar (mM), PBS) and water with a left handed helicity, as observed by transmission electron microscopy (TEM, JEM-1400 available from JEOL).

Intracellular self-assembly of molecules requires a significantly high intracellular concentration of the molecules, as compared with a critical aggregation concentration (CAC). In order to verify whether intracellular self-assembly of the Mito-FF according to the present disclosure can occur or not, the CAC of the Mito-FF was measured as follows.

Intensities of emission at 344 nanometers (nm) and 339 nm in a pyrene excitation spectrum differ according to whether pyrene molecules are present as unaggregated individual molecules or as aggregated molecules. The intensities at 344 nm and 339 nm in the excitation spectrum were measured, and the ratio of an intensity in the excitation spectrum at 344 nm to an intensity in the excitation spectrum at 339 nm was calculated. Based on the standard curve shown in FIG. 4, the CAC for Mito-FF was determined.

Figure 4:
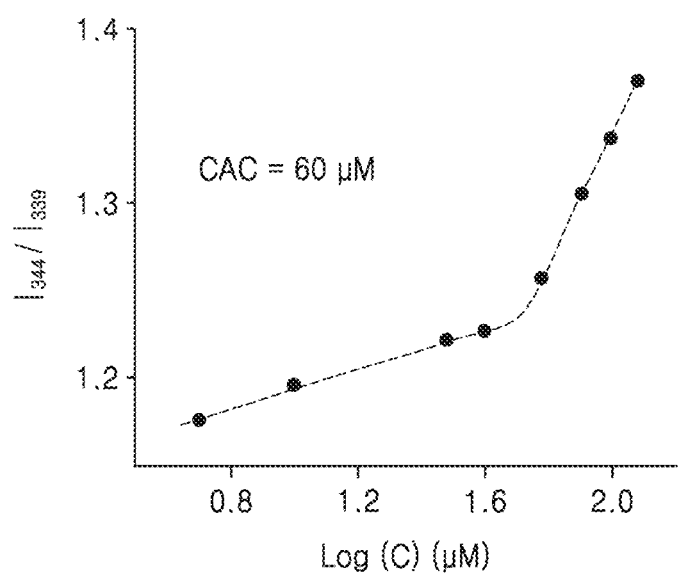
FIG. 4 is a graph of Log (C) (μm) versus (vs.) $I_{344}/I_{339}$, which shows determination of a critical aggregation concentration (CAC) by a pyrene excitation method, according to an embodiment.

As a result, as shown in FIG. 4, the CAC for Mito-FF was 60 micromolar (0).

In consideration of the result of the CAC, in the case that an intracellular concentration of the Mito-FF of the present disclosure is 60 μM or greater, self-assembly of Mito-FF may occur.

To get insight about the self-assembling mechanism of Mito-FF, a molecular simulation was conducted in which Mito-FF was self-assembled via coarse-grained molecular dynamics (CGMS), where radius and length was 2.5 nm and 22 nm respectively. The molecular simulation was performed using Material Studio program available from Accelrys Inc., following the protocol of the manufacturer. The molecular simulation was performed between 2 microseconds (μs) and 1.56 μs, and the analysis thereof was converted to a final frame of 50 nanoseconds (ns).

Figure 5:
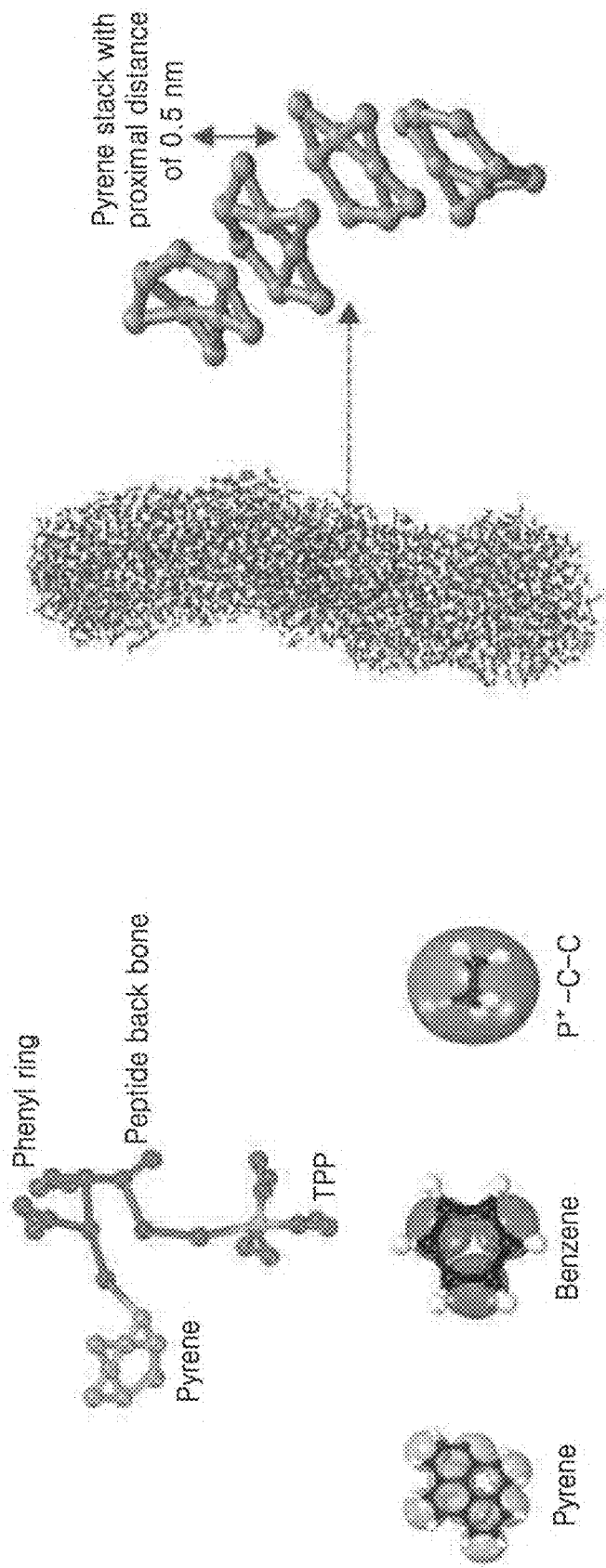
FIG. 5 is a schematic view that illustrates a result of a molecular simulation of Mito-FF via coarse-grained molecular simulation (CGMS), according to an embodiment.

As a result, Mito-FF self-assembled to form helical fiber as shown in right side of FIG. 5. In the self-assembly of Mito-FF, pyrene and phenyl alanine group (Phe) stacked along the fiber with a proximal pyrene-pyrene and Phe-Phe distance of 0.5 nm.

Figure 6:
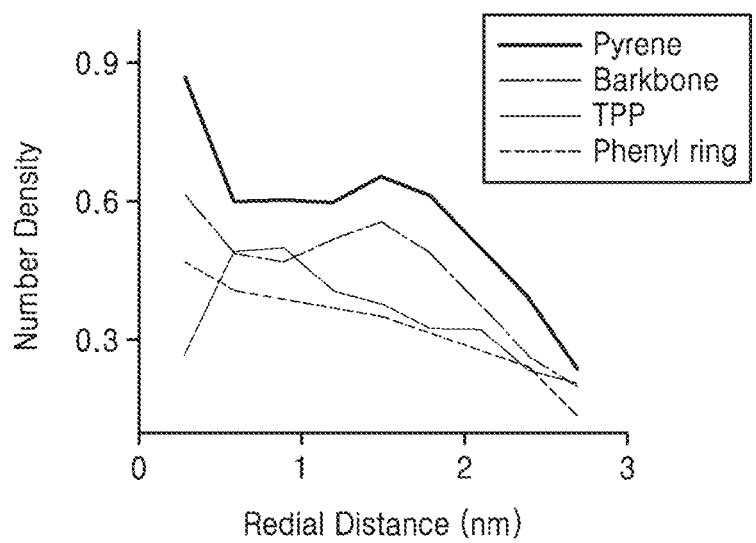
FIG. 6 is a graph of radial distance (nm) vs. number density, which shows a result of analysis of radial number density of Mito-FF, which suggests that a density of each of a phenylalanine group and TPP are high along a surface of fibrils, according to an embodiment.

As shown in FIG. 6, the radial number density analysis showed that the number density of TPP is highest along the surface of the fiber which is then followed by pyrene.

Based on the above result, the driving force for the nanofiber formation of Mito-FF is mainly contributed by the pi-pi interactions among phenylalanine groups as well as pyrene moieties followed by the hydrogen bonding of the peptide backbones.

Figure 7:
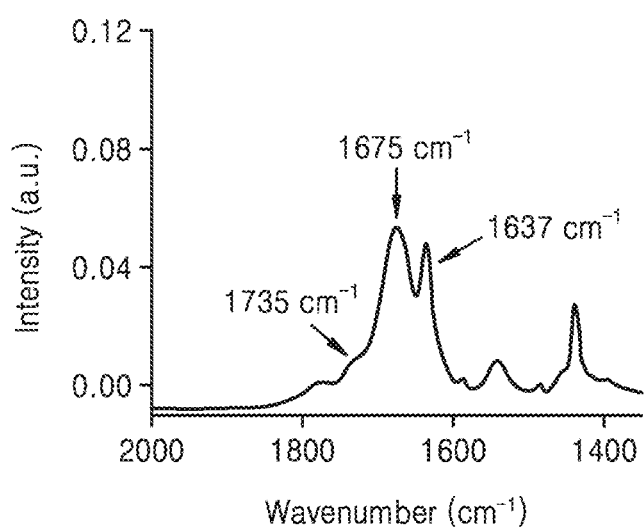
FIG. 7 is a graph of wavenumber vs. intensity (a.u), which shows an FT-IR spectrum of Mito-FF in an attenuated total reflection (ATR) mode, according to an embodiment.

As shown in FIG. 7, FT-IR analysis showed the appearance of amide I peak near 1,637 $cm^{-1}$, indicating the presence of beta sheet structure. Furthermore the peak near 1,675 $cm^{-1}$ confirms the presence of the antiparallel beta conformation of Mito-FF fibrils.

In order to analyze aggregation of Mito-FF by fluorimetric analysis, fluorescence in PBS and MeOH was observed. When pyrene molecules are present as individual molecules, pale blue emission at a wavelength of 400 nm is observed. When pyrene molecules are present as aggregated molecules, a complex is formed in an excited state, and thus sky blue emission at a wavelength of 450 nm is observed. Thus, pyrene emission indicates whether pyrene molecules are in an aggregated state or in an unaggregated individual state.

Figure 8:
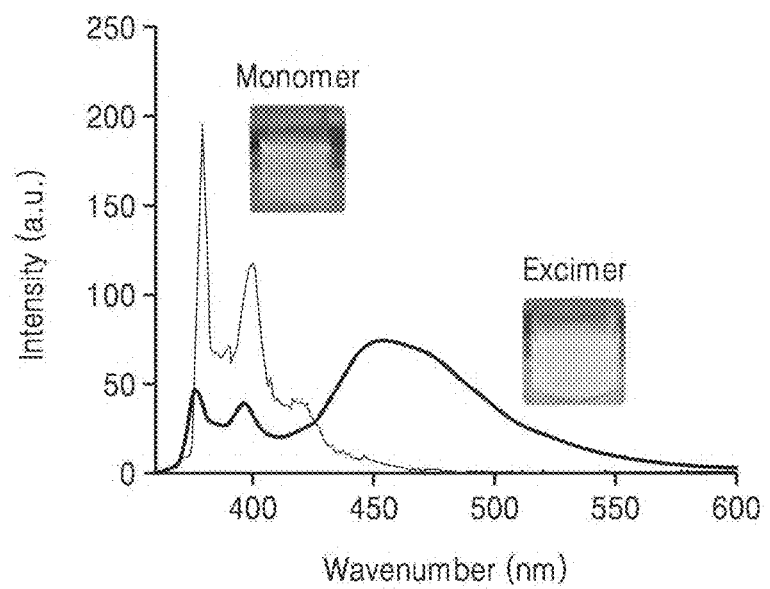
FIG. 8 is a graph of wavelength (nm) vs. intensity (a.u), which shows Mito-FF emission spectra of a monomer and an excimer, according to an embodiment.

As shown in FIG. 8, the spectrofluorimetric analysis of Mito-FF exhibited an intense blue (sky blue) emission at 450 nm in PBS (or water). Accordingly, it was found that Mito-FF forms a pyrene complex (aggregation of Mito-FF), and such fluorescent emission is distinguishable with naked eye under UV lamp as sky blue emission. However, the emission reduced to a pale blue color in MeOH, indicating that pyrene existed in an unaggregated state.

Example 2. Mitochondrial Co-Localization and Mode of Cellular Entry

The presence of TPP conjugated with the Mito-FF of the present disclosure triggers the cellular uptake of the Mito-FF to carcinoma and permeation thereof into mitochondria due to its high negative inner membrane potential.

Mitochondria has a feature of a porous outer membrane and a protein rich inner membrane, which are designed for the tight regulation of its metabolism. These features make the most of the foreign substance failed to enter inside the mitochondria by penetrating its charged membrane. In order to traverse across the membrane, the molecules are required to overcome the activation energy associated with the removal of accompanied water molecules. The molecules with delocalized positive charge are found to lower this activation energy to well penetrate the membrane and enter inside the mitochondria efficiently. The delocalized positive charge over the three phenyl groups, which is stabilized by resonance, facilitates the mitochondrial entry of TPP conjugated molecules.

The process of mitochondrial entry is mainly driven by highly negative inner membrane potential of about −220 mV for carcinoma cells. To confirm the mitochondrial co localization, 20 μm of Mito-FF was incubated with human epithelial carcinoma (HeLa) cells for 1 hour at 37° C., and mitotracker (MitoSOX) red was incubated before 20 minutes of the measurement.

Figure 9:
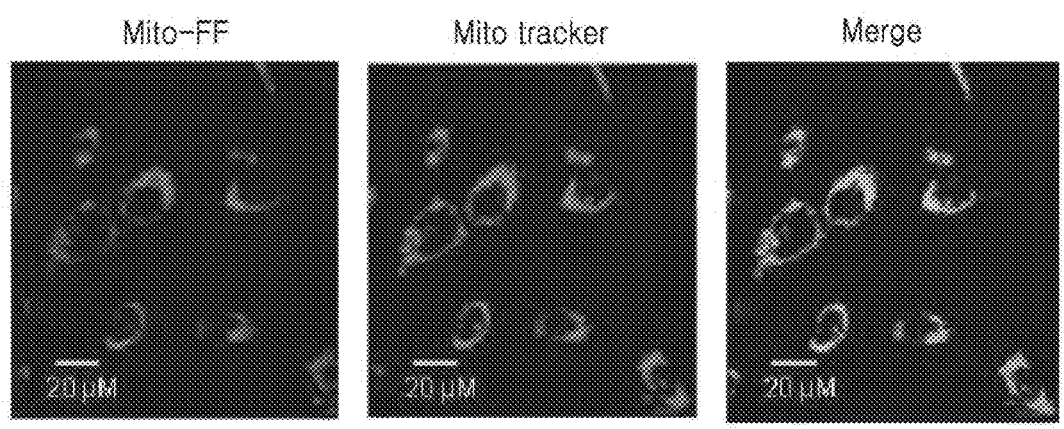
FIG. 9 shows electron micrographs that show cell internalization of Mito-FF in HeLa cells, in which the upper images are the results when performed at a temperature of 37° C., and the lower images are the results when performed at a temperature of 4° C., according to an embodiment.

The results of the analysis using confocal microscopy (LSM-780 available from Zeiss) are shown in FIG. 9. FIG. 9 shows that an overlap between the red fluorescence of the mitotracker (MitoSOX) and blue fluorescence of Mito-FF, which confirms the effective localization in the mitochondria. Moreover, the fluorescence from the lyso-tracker does not exhibit any overlap with the fluorescence from the Mito-FF, implying that colocalization is specific for the mitochondria.

The cellular uptake analysis at 4° C. showed similar observation, suggesting that the peptide enters via an energy independent pathway. This denote that the Mito-FF diffuse through the plasma membrane and readily uptaken by the cells, which is an additional advantage for the small molecule-based drugs, while the assembled structure or high molecular weight molecules generally enter inside the cells via complex energy required mechanism such as endocytosis.

Example 3. Intra-Mitochondrial Assembly

Figure 10:
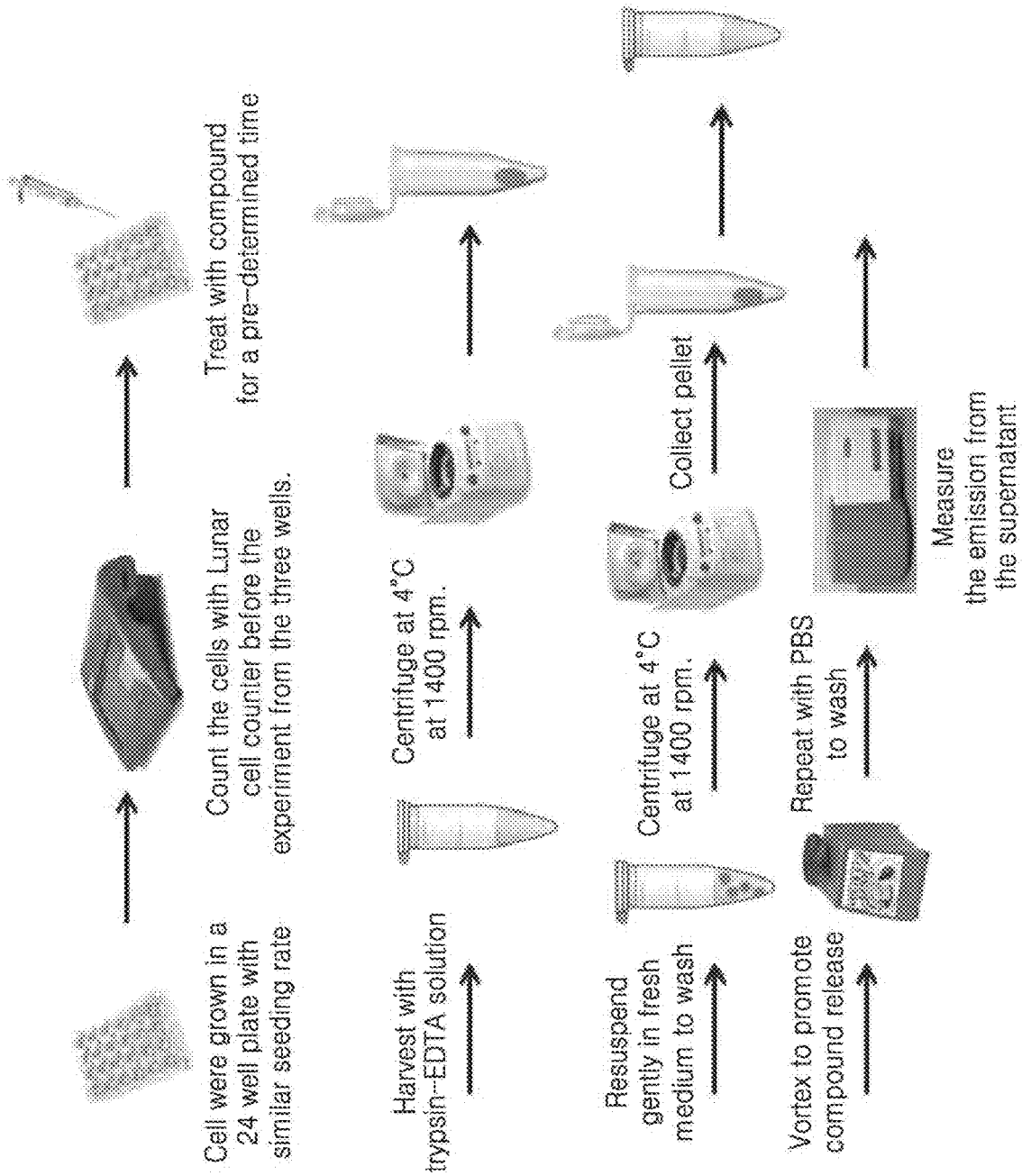
FIG. 10 is a schematic view that illustrates determination of mitochondrial accumulation, according to an embodiment.

Since the process of self-assembly is entirely driven by a molecular concentration, it is critical to examine the concentration of Mito-FF inside mitochondria. The local concentration of Mito-FF in the mitochondria was measured by using concentration-dependent emission spectra of Mito-FF. The measurement of the concentration of the Mito-FF in the mitochondria was measured as follows. The schematic diagram for the measurement procedure is shown in FIG. 10.

The Mito-FF was incubated with HeLa cells for 3 hours, and the cellular uptake was examined after complete lysis of the cells. Subsequently, the emission spectra was examined, and comparison with the calibration plot of Mito-FF under similar condition was performed. The confocal imaging analysis with Mito-FF showed that the Mito-FF localizes inside the mitochondria, which implies that the Mito-FF obtained with the cell lysate is entirely from mitochondria.

Figure 11:
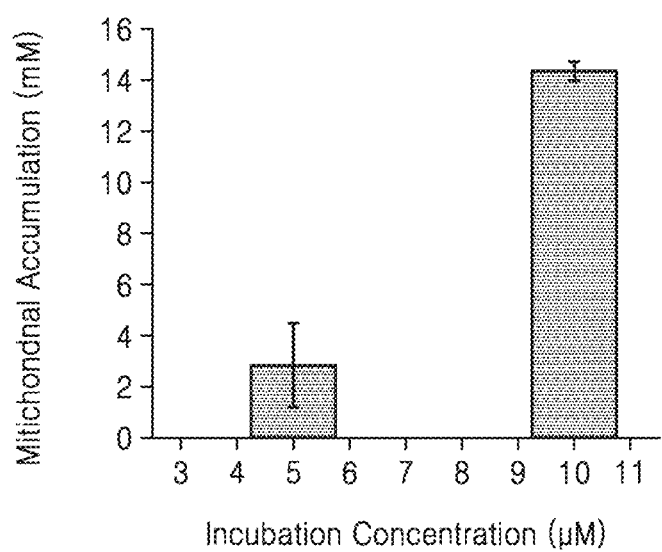
FIG. 11 is a graph of incubation concentration (mM) vs. mitochondrial accumulation (0), which shows mitochondrial accumulation of Mito-FF in HeLa cells, according to an embodiment.

As shown in FIG. 11, the self-assembly of Mito-FF inside a mitochondrion may readily occur because of a concentration of Mito-FF of several mM inside the mitochondrion, which may be significantly higher than the CAC.

In order to get further evidence for the mitochondrial assembly, a two-photon confocal analysis was performed on HeLa cells after incubation with Mito-FF.

The two photons have approximately half of the energy (and double the wavelength) of the photon required for a single photon excitation quantum event to occur. Since the maximum pyrene excitation wavelength is around 343 nm, the excitation wavelength was set at 780 nm, and the emission from the HeLa cells after treatment with Mito-FF was analyzed.

Pyrene is a molecular probe that has been employed for deep study of several biomolecules, including proteins, lipids, nucleic acids, and bio membranes, due to its unique spectroscopic and photophysical properties. Pyrene has been widely used to exploit information about protein structure, molecular organization, and conformation. Due to this property of pyrene that allows pyrene to serve as an indicator of self-assembly inside mitochondria, Mito-FF was conjugated with pyrene.

A notable feature for pyrene fluorescent emission employed for biomolecule conformational analysis is appearance of an unstructured band at longer wavelengths in a range of 420 nm to 480 nm, when two pyrenes are separated by a distance of at least 10 A ° from each other.

Figure 12:
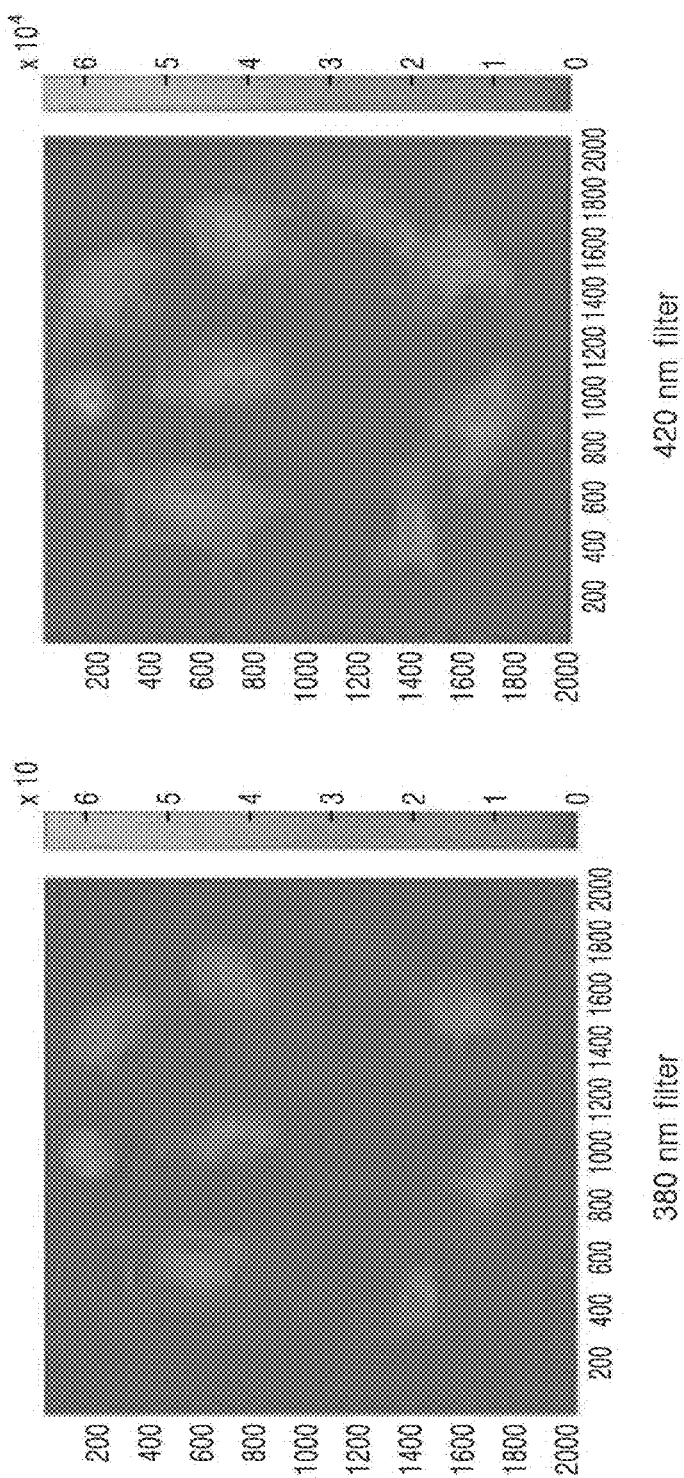
FIG. 12 shows the results of two-photon confocal analysis performed on HeLa cells treated with Mito-FF, which suggest that a density at a filter range of 420 nm to 480 nm, i.e., an excimer emission range, is higher than that at a filter range of 380 nm to 420 nm, i.e., a monomeric emission range, according to an embodiment.

As shown in FIG. 12, as a result of the two-photon confocal analysis, the CGMS molecular simulation of Mito-FF showed that during the assembly of Mito-FF, two pyrenes oriented toward each other with a proximity of 0.5 nm. Thus, in light of the bright emission at 420 nm, it was found that an excited state dimer was formed upon excitation.

The blue emission observed during the confocal analysis of HeLa cells treated with Mito-FF as shown in FIG. 9 may belong to the excimeric pyrene, since the wavelength was about 410 nm. For the statistical evaluation of the ratio of excimeric emission to monomeric emission from the HeLa cells treated with Mito-FF, two-photon confocal microscopic analyses were performed, which in turn provided an insight about assembly as well as local concentration of Mito-FF inside mitochondria.

Figure 13:
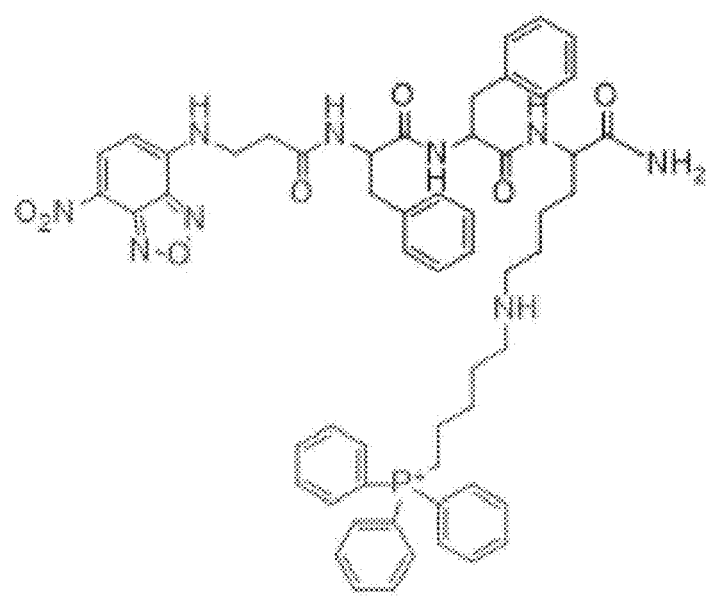
FIG. 13 is a schematic view that illustrates a molecular structure of Mito-FF-NBD, according to an embodiment.

To further support the assembly of Mito-FF inside mitochondria, another peptide has been synthesized, that is, Mito-FF-NBD. As shown in FIG. 13, pyrene is replaced with another environment sensitive dye; 4-nitro-2,1,3-benzoxadiazole (NBD).

The NBD dye is a fluorophore known to produce more intense fluorescence in a hydrophobic environment than in a hydrophilic environment, and has been used in imaging studies of biological components. Due to this property, the NBD dye may be used in examining formation of fibers inside a cell.

In order to confirm fibrous assembly inside mitochondria, Mito-FF and Mito-FF-NBD were co-incubated with HeLa cells for 3 hours, followed by observation using confocal microscopy as in Example 2.

Figure 14:
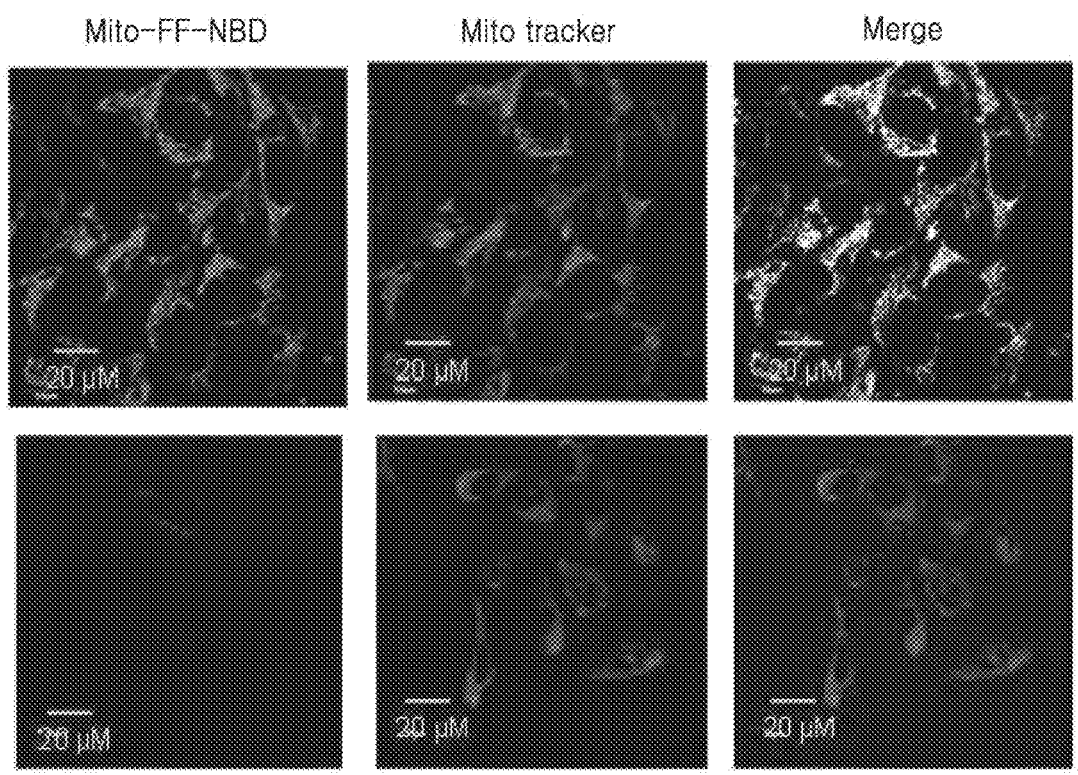
FIG. 14 shows electron micrographs, in which the upper images show Mito-FF co-assembly with Mito-FF-NBD inside mitochondria emitting bright green fluorescence when Mito-FF was co-incubated with Mito-FF-NBD in HeLa cells; and the lower images show that co-assembly was not achieved when Mito-FF-NBD was incubated in HeLa cells, according to an embodiment.

As a result, as shown in FIG. 14, in the case of co-incubation of Mito-FF and Mito-FF-NBD, bright emission was observed. However, such bright emission was absent with Mito-FF-NBD alone.

This result shows that Mito-FF-NBD co-assembles with Mito-FF fibrils in which NBD may essentially be exposed towards a hydrophobic environment which results in bright fluorescence. However in the absence of Mito-FF, Mito-FF-NBD does not form fibrils, which consequently fails to result in fluorescence.

For solid proof of mitochondrial assembly, a mitochondrion was isolated from HeLa cells according to a known protocol. 100 μg of mitochondria were co-incubated with 10 μM of Mito-FF at a temperature of 37° C. In a control group, 100 μg of mitochondria was incubated without Mito-FF at a temperature of 37° C. Subsequently, the mitochondria were observed by using TEM as in Example 1.

Figure 15:
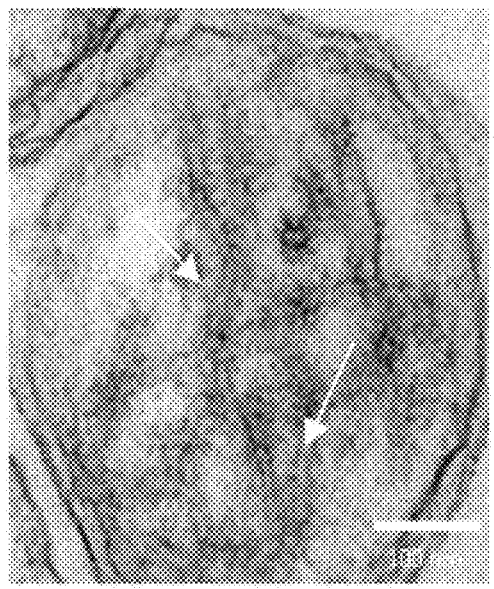
FIG. 15 is a TEM image that shows Mito-FF fibril formation in a mitochondrion of a cell taken from a mouse, according to an embodiment.

As a result, as shown in FIG. 15, the TEM image shows that fibrils were formed inside the mitochondrion.

The TEM image shown in FIG. 15 shows not only the Mito-FF fibrils formed inside but also the mitochondrial membrane including cristae destroyed by the fibrils, as compared with the control group which appeared to have spherical morphology with well-defined cristae. This result indicates that the fibrils may induce significant dysfunction of mitochondrial metabolism and eventually damage the whole cell.

Figure 16:
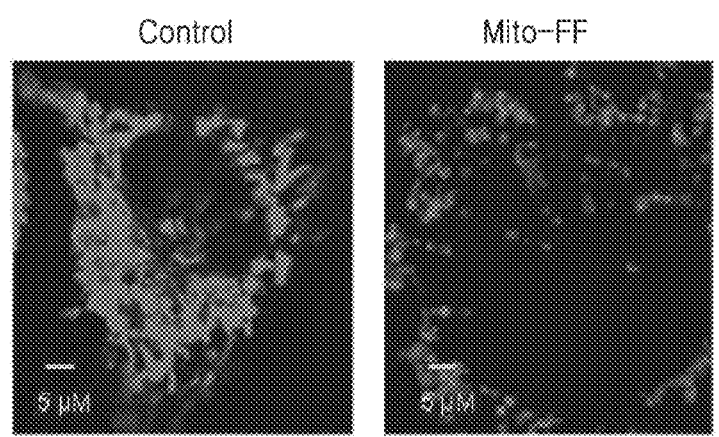
FIG. 16 shows confocal micrographs showing shrinkage of a mitochondrion treated with Mito-FF, as compared with a control group, as a result of confocal microscopic analysis, according to an embodiment.

Example 4. Mitochondrial Dysfunction Caused by Mito-FF Fibrils and Cancer Cell-Specific Cytotoxicity As shown in FIG. 16, a confocal image of a mitochondrion of a HeLa cell after treatment with Mito-FF shows that mitochondrion morphology was severely deformed and damaged, as compared with a control group.

To confirm the mitochondrial dysfunction by the treatment with Mito-FF, the ability of Mito-FF to induce mitochondrial membrane potential depolarization was investigated with tetramethyl rhodamine dye (TMRM) which shows bright fluorescence under normal conditions and vanishes in accordance with the depolarization of the membrane. Under normal conditions, the inner membrane of mitochondria is in an electrochemically polarized state with a higher concentration of $H^+$ in the inner membrane space. The electrochemical gradient across the membrane causes $H^+$ to flow to the inner membrane of mitochondria and this process is coupled with production of adenosine triphosphate (ATP). The external materials which may uncouple this process cause the flow of $H^+$ to be independent of ATP production. This condition is referred as mitochondrial depolarization, which serves as a preliminary indication of mitochondrial dysfunction.

Figure 23:
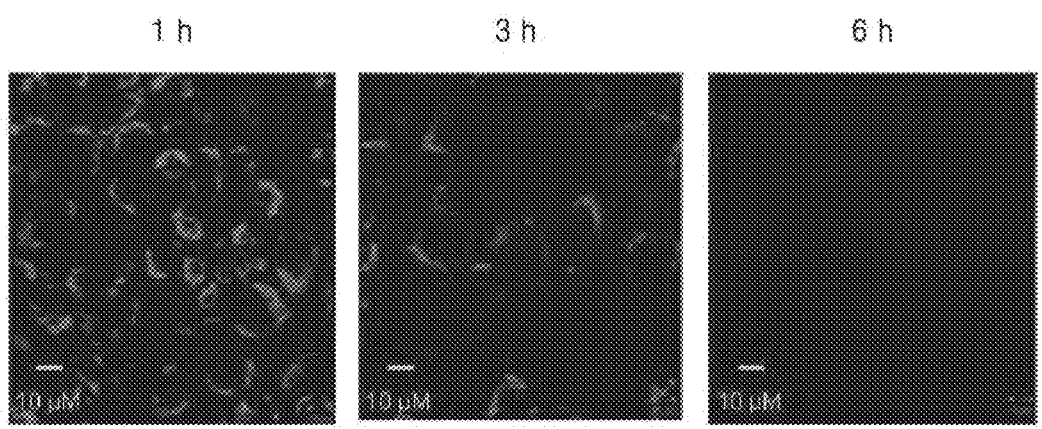
FIG. 23 shows electron micrographs that show measurement results of membrane depolarization of HeLa cells treated with TMRM and Mito-FF, measured in a time-dependent manner, according to an embodiment.

To examine the effect of Mito-FF on the mitochondrial membrane potential, HeLa cells were incubated with TMRM and Mito-FF. The fluorescence emission from the TMRM was monitored at times lapses of 1 hour, 3 hours, and 6 hours. Red fluorescence of TMRM appears when a mitochondrial membrane is completely polarized, whereas depolarization of a mitochondrial membrane causes disappearance of TMRM red fluorescence. The Mito-FF treated with TMRM, showed significant red fluorescence after 1 hour of incubation, which started diminishing after 3 hours and completely vanished within 6 hours. The results thereof are shown in FIG. 23. This observation indicates that formation of Mito-FF fibrils depolarizes a mitochondrion, and adversely affects function thereof.

The mitochondrial dysfunction may result in excessive production of reactive oxygen species (ROS). To confirm the oxidative stress induced by Mito-FF, generation of ROS within mitochondria was monitored using Mito SOX Red. Mito SOX Red is a fluorogenic dye which selectively and rapidly accumulates in mitochondria, is oxidized by superoxide, and exhibits red fluorescence.

Figure 17:
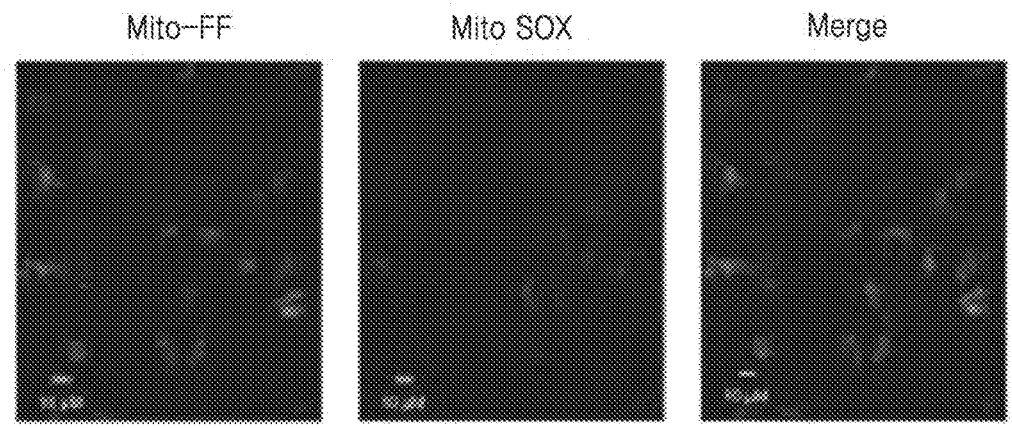
FIG. 17 shows electron micrographs that show ROS generation in mitochondria of HeLa cells measured by using Mito Sox, according to an embodiment.

As shown in FIG. 17, the red fluorescence, which appeared from Mito SOX Red after 6 hours of incubation of Mito-FF with HeLa cells, implies that the ROS was generated inside the mitochondria.

The mitochondrial stress may eventually lead to the whole-cell stress. To confirm this expectation, the ROS generation analysis within the cell was performed using dihydroethidium (DHE) dye. DHE dye may intercalate with nuclear DNA and oxidizes to ethidium in the presence of ROS, which may show red fluorescence.

Figure 18:
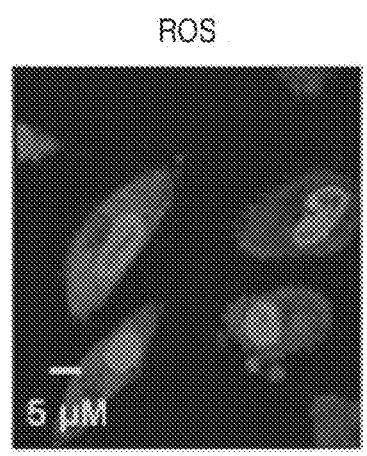
FIG. 18 is an electron micrograph that shows generation of significant ROS in HeLa cells incubated with Mito-FF fibrils confirmed by using DHE, according to an embodiment.
Figure 19A:
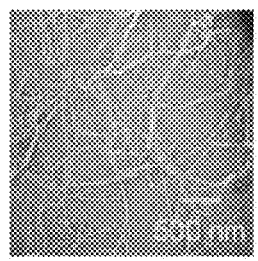
FIG. 19A is a TEM image of Mito-VV incubated with HeLa cells, according to an embodiment.
Figure 19B:
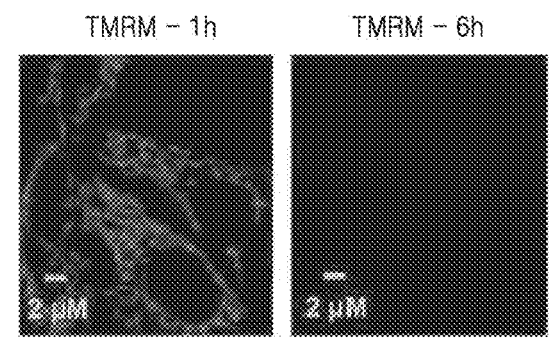
FIG. 19B is a TEM image of Mito-FxFx incubated with HeLa cells, according to an embodiment.
Figure 19C:
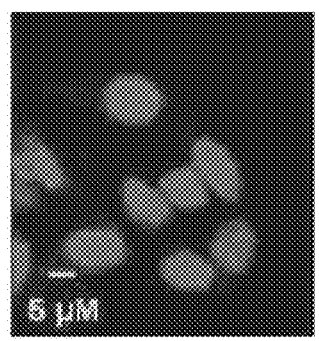
FIG. 19C shows measurement results of time-lapse fluorescence emission of Mito-VV from TMRM monitored at 1 hour and 6 hours, according to an embodiment.
Figure 19D:
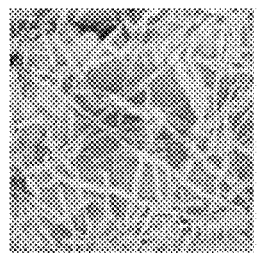
FIG. 19D shows measurement results of time-lapse fluorescence emission of Mito-FxFx from TMRM monitored at 1 hour and 6 hours, according to an embodiment.
Figure 19E:
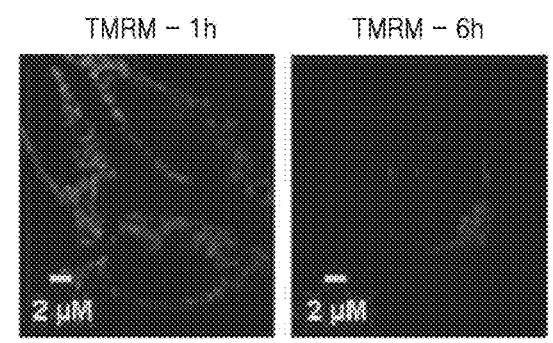
FIG. 19E shows results of ROS generation analysis of the HeLa cells incubated with Mito-VV by using DHE, according to an embodiment.
Figure 19F:
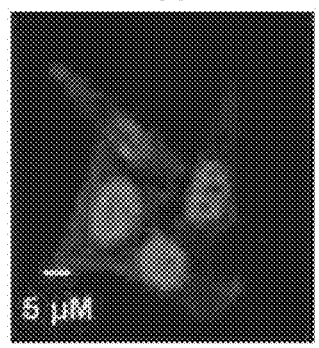
FIG. 19F shows results of ROS generation analysis of the HeLa cells incubated with Mito-FxFx by using DHE, according to an embodiment.

As shown in FIG. 18, in consideration of red fluorescence of DHE within the whole cell, it was found that significant ROS was generated in the HeLa cells incubated with Mito-FF fibrils upon treatment with Mito-FF.

Figure 25:
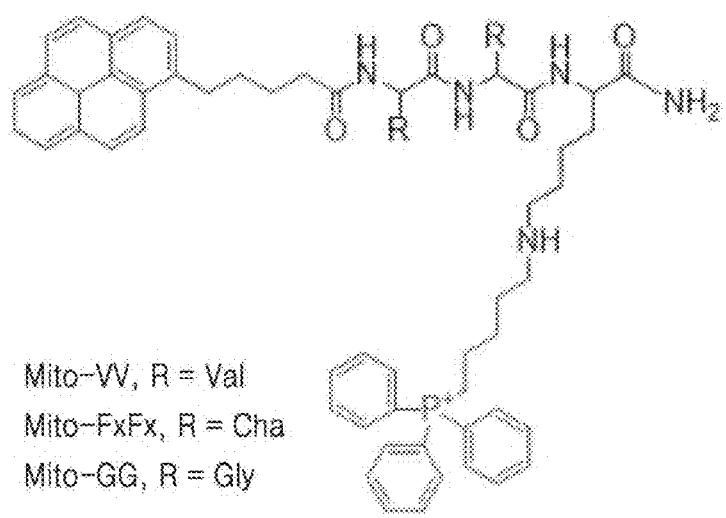
FIG. 25 illustrates a molecular structure of a control peptide according to an embodiment.

Phenylalanine is well known to be important for the acceleration of the amyloid assembly process in Alzheimer's disease (AD) and other amyloid diseases by formation of toxic fibril aggregates. To investigate whether mitochondrial damage caused by fibril formation is specific for phenylalanine fibrils, the molecular design used in the experiment was extended to Mito-VV and Mito-FxFx, where the phenylalanine is replaced by valine and cyclohexylalanine, respectively, as shown in FIG. 25.

TEM images of Mito-VV and Mito-FxFx were obtained by observation in the same manner as in Example 3. Then, in the same manner as described above, the time-lapse fluorescence emission from the TMRM was monitored at 1 hour and 6 hours, and the ROS generation analysis within the cell was performed using DHE dye.

As a result, as shown in FIG. 19, when HeLa cells treated with Mito-VV and Mito-FxFx, red fluorescence of TMRM disappeared within 6 hours, followed by the ROS generation as evidenced by the Mito Sox and DHE. Accordingly, it was found that mitochondrial damage caused by fibril formation is not specific for phenylalanine fibrils.

In order to verify the result in another manner, Mito-GG, in which phenylalanine is replaced with glycine, was prepared. In the same manner as in Example 1, it was found that Mito-GG has a CAC of 114 μM or greater, by using a pyrene excitation spectrum, and showed a micellar-like structure of size below 50 nm, which was measured by using electron microscopy.

Figure 20A:
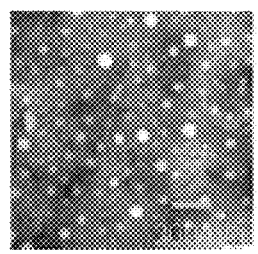
FIG. 20A is a TEM image of Mito-GG incubated with HeLa cells, according to an embodiment.
Figure 20B:
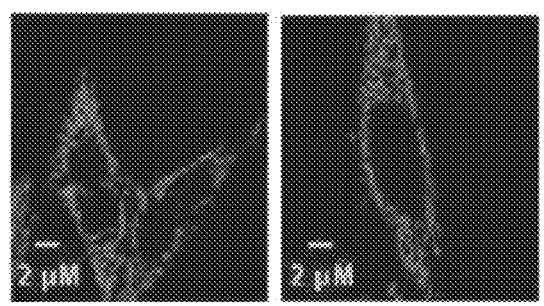
FIG. 20B shows measurement results of time-lapse fluorescence emission of Mito-GG from TMRM monitored at 1 hour and 6 hours, according to an embodiment.
Figure 20C:
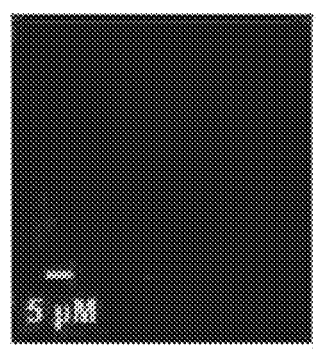
FIG. 20C shows results of ROS generation analysis in the HeLa cells incubated with Mito-GG by using DHE, according to an embodiment.

As shown in FIG. 20, as a result of an experiment on Mito-GG, performed in the same manner as in experiments on Mito-VV and Mito-FxFx, when Mito-GG was incubated with HeLa cells, the red fluorescence of TMRM did not disappear even after 6 hours of incubation with HeLa cells, unlike other fibril aggregates. In addition, little ROS was generated.

Accordingly, in the case that small micelles are formed like Mito-GG, the mitochondrial stress induced by the small micelles might be low, as compared with Mito-VV and Mito-FxFx. Thus, in this case, it is less likely to cause mitochondrial dysfunction.

To visualize the mitochondrial dysfunction induced by Mito-FF, a TEM image analysis was conducted with HeLa cells treated with Mito-FF of a concentration of 20 μM for 3 hours in the same manner as in Example 3.

Figure 21:
FIG. 21 is a TEM image that shows a severely damaged mitochondrion after treatment with Mito-FF, according to an embodiment.

As a result, as shown in FIG. 21, most of the mitochondrion was severely damaged after treatment with Mito-FF. In the TEM image to the right side of FIG. 21, it is clearly shown that fibrils were formed inside the mitochondrion, the fibrils penetrating outwards through the mitochondrial membrane.

Accordingly, it was found that the fibril formation inside the mitochondrion induced the disruption of the mitochondrial membrane and thereby entirely damaged the organelle.

Figure 22:
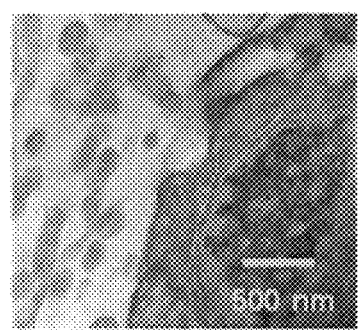
FIG. 22 is a TEM image that shows an undamaged mitochondrion after treatment with Mito-GG, according to an embodiment.

However, as shown in FIG. 22, the mitochondrion of the HeLa cells treated with Mito-GG remained unaffected under similar conditions, as shown in the TEM image.

After the confirmation of the intra-mitochondrial assembly of peptide amphiphile, the toxicity of Mito-peptides toward a variety of cells was analyzed, the cells including cancer cell lines such as HeLa (ATCC, cervical cancer), MDA-MB-486 (ATCC) (mammary cancer) MCF10 (breast cancer), PC3 (ATCC, prostate cancer), SCC7 (ATCC, skin cancer), HEK293T (ATCC), and NIH-3T3 (ATCC).

In order to analyze cell cytotoxicity, the cancer cells were incubated in an incubator including a DMEM medium (available from Gibco) containing 10% of FBS, 1% of penicillin/streptomycin (available from Life Technologies) at a temperature of 37° C. Cell viability thereof was measured 24 hours after cell incubation, by following the protocol of the manufacturer of Alamar Blue assay (available from Thermo Fisher Scientific).

As a result of the experiment, as shown in FIG. 33, Mito-FF, Mito-FxFx, and Mito-VV peptides each had an $IC_{50}$ of 10 μM; however, Mito-GG had a significantly low $IC_{50}$, as compared with the other peptides. Accordingly, it was found that Mito-GG has low cell cytotoxicity, as compared with the other peptides.

Multidrug resistance, the principal mechanism by which many cancers develop resistance to chemotherapy drugs, is a major factor in the failure of many forms of chemotherapy. This resistance exists against every effective anticancer drug and may develop by numerous mechanisms including decreased drug uptake, increased drug efflux, activation of detoxifying systems, activation of DNA repair mechanisms, and evasion of drug-induced apoptosis, etc.

Figure 24:
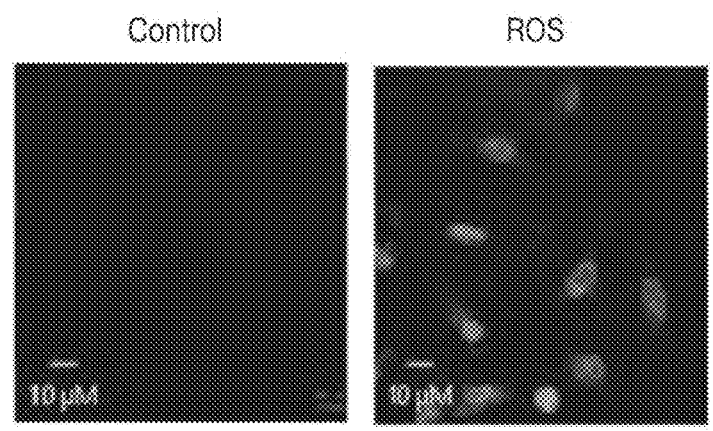
FIG. 24 shows electron micrographs that show measurement results of ROS generation using DHE, as compared with a control group, according to an embodiment.

According to FIG. 23, which shows TMRM after the treatment with Mito-FF with respect to time, and FIG. 24, which shows ROS generation, in the case that a drug resistance cell line (MCF7/ADR cell) was treated with Mito-peptides, cell cytotoxicity against the cells was significant.

A cell requires some time to have enough accumulation inside mitochondria for fiber formation, but once fiber is formed inside the mitochondria, the cell starts malfunctioning and finally apoptosis is induced.

In order to confirm whether apoptosis occurs or not by treatment with Mito-peptides, the cell viability of HEK 293T normal cell lines treated with Mito-FF, Mito-FxFx, Mito-VV, or Mito-GG was measured in the same manner as described above.

Figure 29:
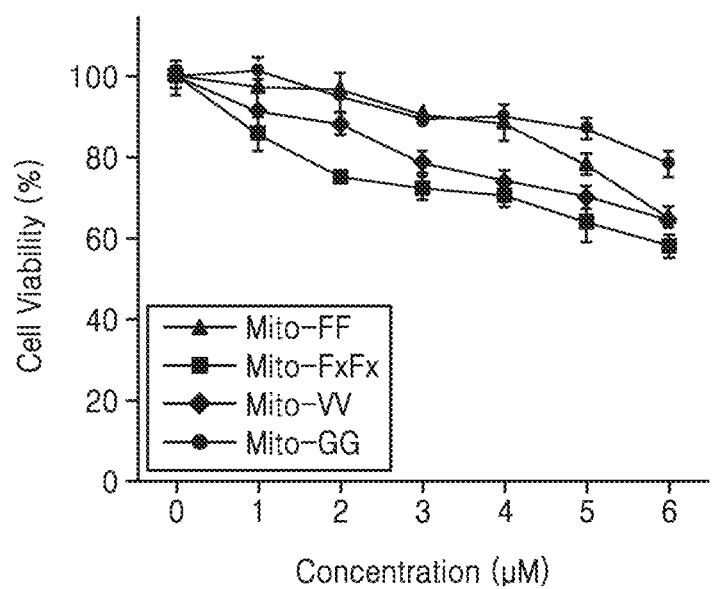
FIG. 29 is a graph of concentration ($\mu$M) vs. cell viability, which shows measurement results of cell viability after incubation of HEK293T cells for 24 hours, according to an embodiment.
Figure 30:
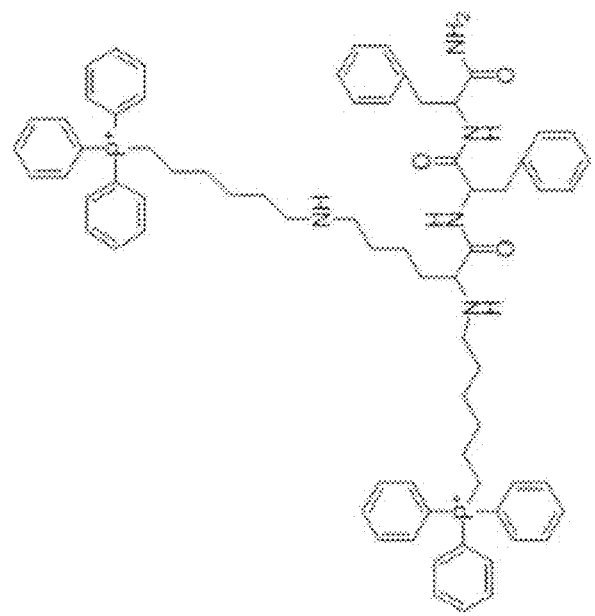
FIG. 30 is a schematic view that illustrates molecular structures of peptides bound to TPP, according to an embodiment.
Figure 30:
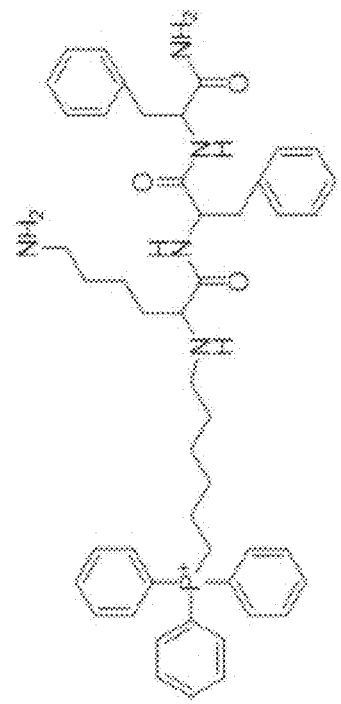

As a result, as shown in FIG. 29, the Mito-peptides showed only a 20% reduction in the cell viability in HEK 293T normal cell lines treated with Mito-peptides. The non-toxicity against normal cell lines is in accordance with the reduced accumulation of Mito-FF inside HEK 293T mitochondria, in which the membrane potential is less negative than that of carcinoma cells.

Accordingly, since penetration of Mito-peptides into normal cells is relatively smaller than that into carcinoma cells, it was found that the Mito-peptides had no toxicity against normal cells even after 24 hours of treatment.

TPP molecules are rapidly and extensively taken in by mitochondria and have been found to have a toxic effect on mitochondrial function. In order to see whether the number of TPP molecules has an impact on the toxicity, a phenylalanine dipeptide was synthesized, the phenylalanine dipeptide being conjugated with one TPP molecule (on the left side) and two TPP molecules (on the right side).

Figure 31:
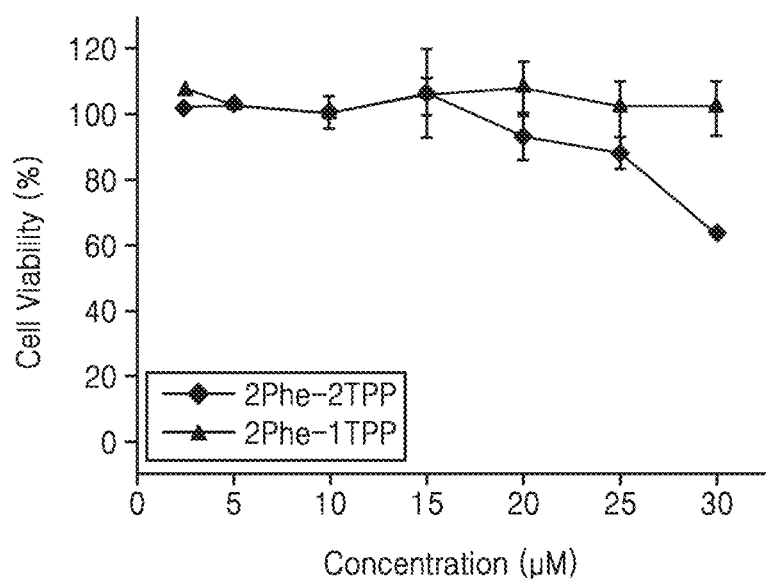
FIG. 31 is a graph of concentration ($\mu$M) vs. cell viability, which shows measurement results of cell viability of the peptides bound to TPP, which suggest that the peptides have no cytotoxicity, according to an embodiment.

All peptides formed micellar morphology with a size of 50 nm or less. As shown in FIG. 31, similar to the results of the foregoing experiment, both the phenylalanine dipeptide conjugated with one TPP molecule and the phenylalanine dipeptide conjugated with two TPP molecules did not induce any toxicity against cancer cell lines.

Figure 32:
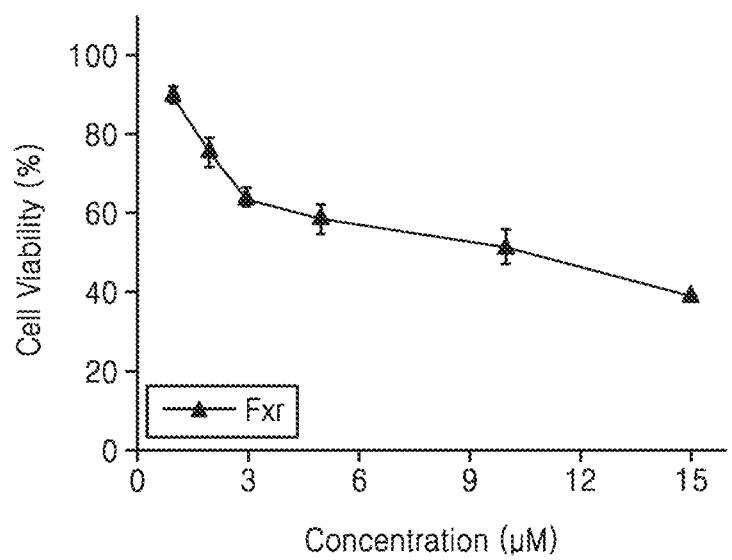
FIG. 32 is a graph of concentration ($\mu$M) vs. cell viability, which shows measurement results of cell viability after incubating Fxr peptide in HELa cells for 24 hours, according to an embodiment.
Figure 33A:
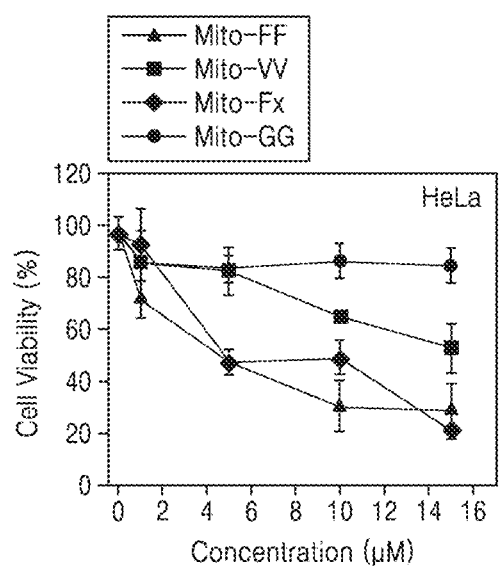
FIG. 33A shows a graph of concentration ($\mu$M) vs. cell viability, which shows cytotoxicity of Mito-peptides against a variety of cell lines, according to an embodiment.
Figure 33B:
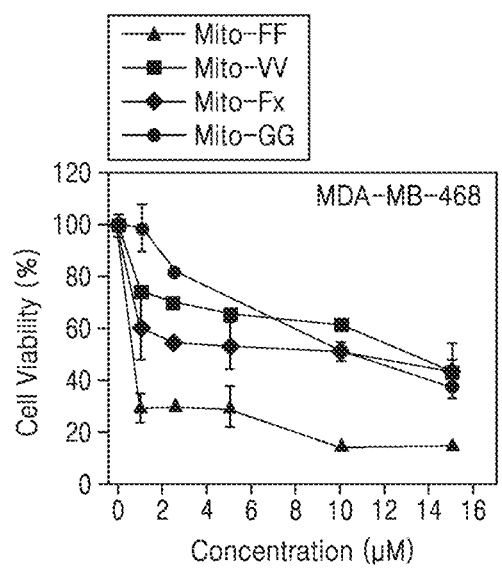
FIG. 33B shows a graph of concentration ($\mu$M) vs. cell viability, which shows cytotoxicity of Mito-peptides against a variety of cell lines, according to an embodiment.
Figure 33C:
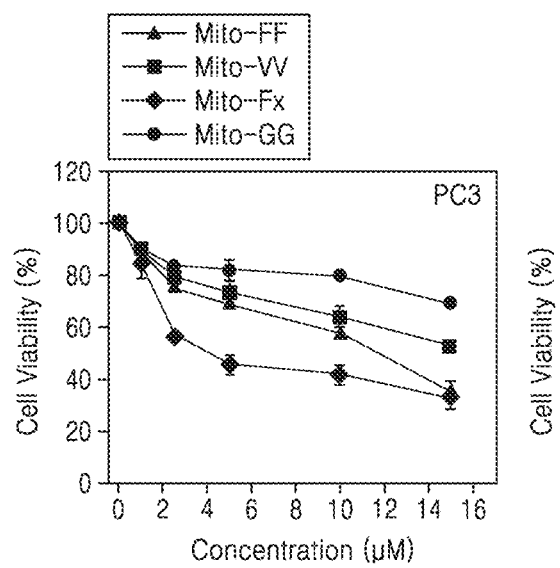
FIG. 33C shows a graph of concentration ($\mu$M) vs. cell viability, which shows cytotoxicity of Mito-peptides against a variety of cell lines, according to an embodiment.
Figure 33D:
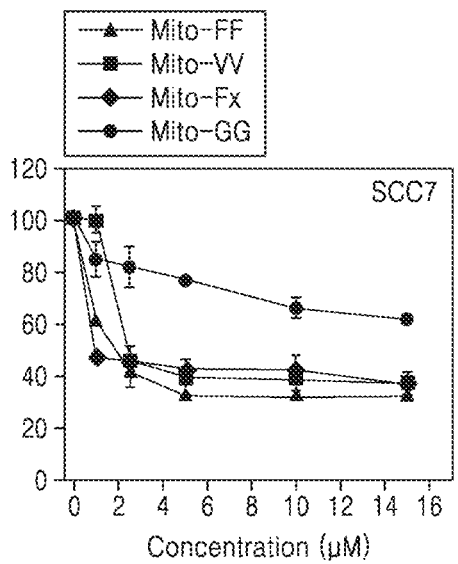
FIG. 33D shows a graph of concentration ($\mu$M) vs. cell viability, which shows cytotoxicity of Mito-peptides against a variety of cell lines, according to an embodiment.
Figure 33E:
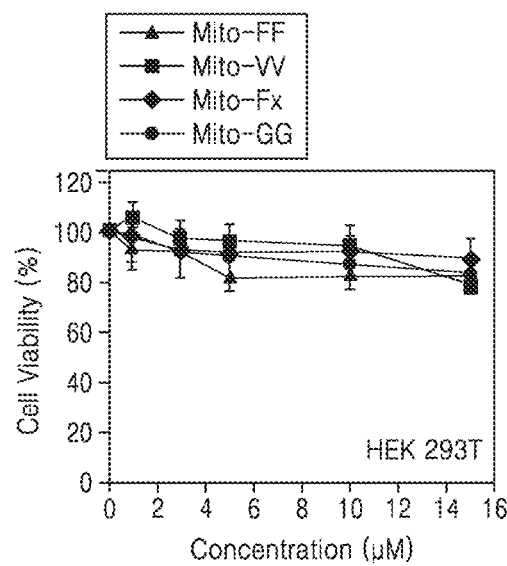
FIG. 33E shows a graph of concentration ($\mu$M) vs. cell viability, which shows cytotoxicity of Mito-peptides against a variety of cell lines, according to an embodiment.
Figure 33F:
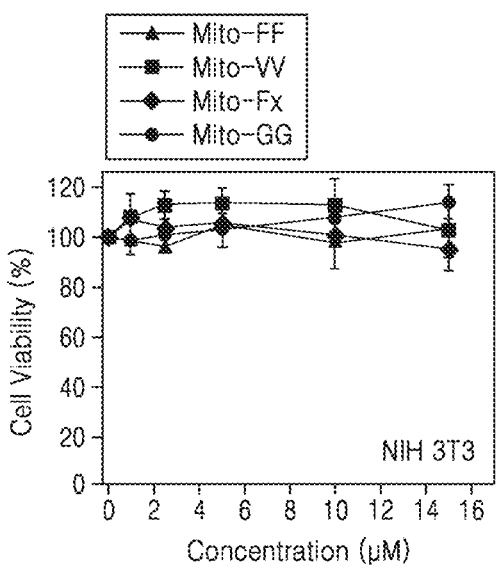
FIG. 33F shows a graph of concentration ($\mu$M) vs. cell viability, which shows cytotoxicity of Mito-peptides against a variety of cell lines, according to an embodiment.

To further support this result, another peptide was formed. The formed peptide was Fxr (having a sequence of pyrene-FFKFxrFxr), which was conjugated with no TPP molecules. However, this peptide formed a fibril structure. Due to its high positive charge, the peptide localized inside the mitochondria. As shown in FIG. 32, the toxicity analysis in HeLa cells showed significant toxicity.

Mitochondria play a vital role in the initiation of an intrinsic apoptosis cascade. It was anticipated that a Mito-peptide localized in a mitochondrion may self-assemble, thereby causing stress in the mitochondrion and inducing apoptotic mechanisms. To confirm this prediction experimentally, FITC annexin/PI staining assay was performed.

For the FIIC annexin/PI staining assay, HeLa cells were incubated in an incubator including a DMEM medium (available from Gibco) containing 10% of FBS and 1% of penicillin/streptomycin (available from Life Technologies) at a temperature of 37° C. 10 μM of each peptide was incubated for 1, 4, 6, 8, or 10 hours. Following the protocol of the manufacturer, the cells were incubated for 15 minutes at room temperature in the presence of 100 μL of annexin-binding buffer solution, 5 μL of Alexa Fluor 488-conjugated annexin V (V13241 available from Life Technologies), and 1 μL of a 100 μg/mL PI working solution. After the incubation, the stained cells were observed with a confocal microscopy as in Example 2.

Figure 34:
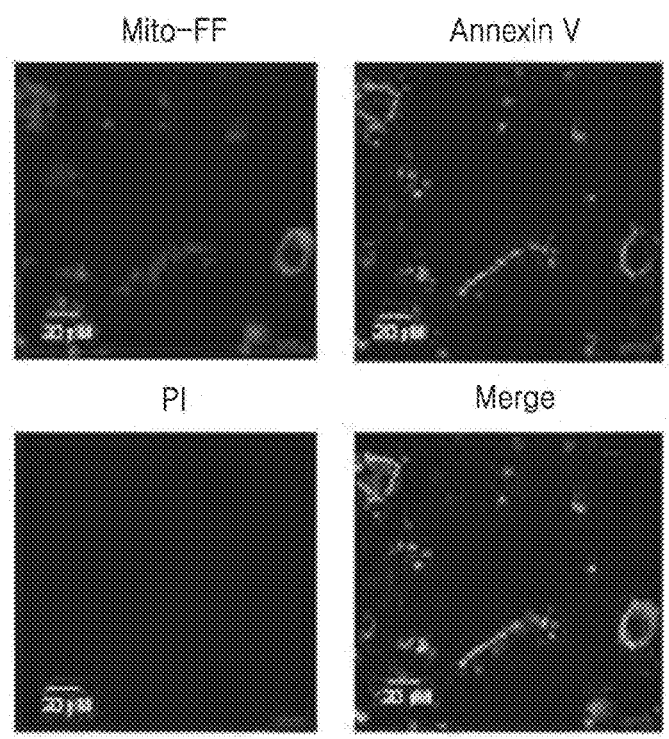
FIG. 34 shows electron micrographs that show measurement results of cell death induced by Mito-FF by using an Annexin V/PI staining assay, which suggest that the cell death occurs by early apoptosis, according to an embodiment.

As a result, as shown in FIG. 34, Annexin V was able to stain the plasma membrane of HeLa cells treated with Mito-FF, but PI was not. The membrane-impermeable PI may be used in distinguishing live or early apoptotic cells from late apoptotic or necrotic cells that lose membrane integrity. Annexin V stains both apoptotic cells which expose phosphatidylserine extracellularly and necrotic cells which lose membrane integrity, but PI does not. The live cells exclude both of the dyes from staining, whereas the necrotic cells allow staining by both of the dyes. The results of this experiment shown in FIG. 34 shows that the cells entered an early apoptotic stage within 6 hours of treatment with Mito-FF.

For the quantitative analysis of apoptosis, flow cytometric analysis (FACS) was conducted over time with FI-TC annexin V/PI staining assay by using FACSCalibur (available from BD Bioscience), following the protocol of the manufacturer.

In detail, HeLa cells treated with 10 μM of Mito-FF were incubated for 4 hours or 8 hours. Then, FACS analysis was performed thereon.

Figure 35:
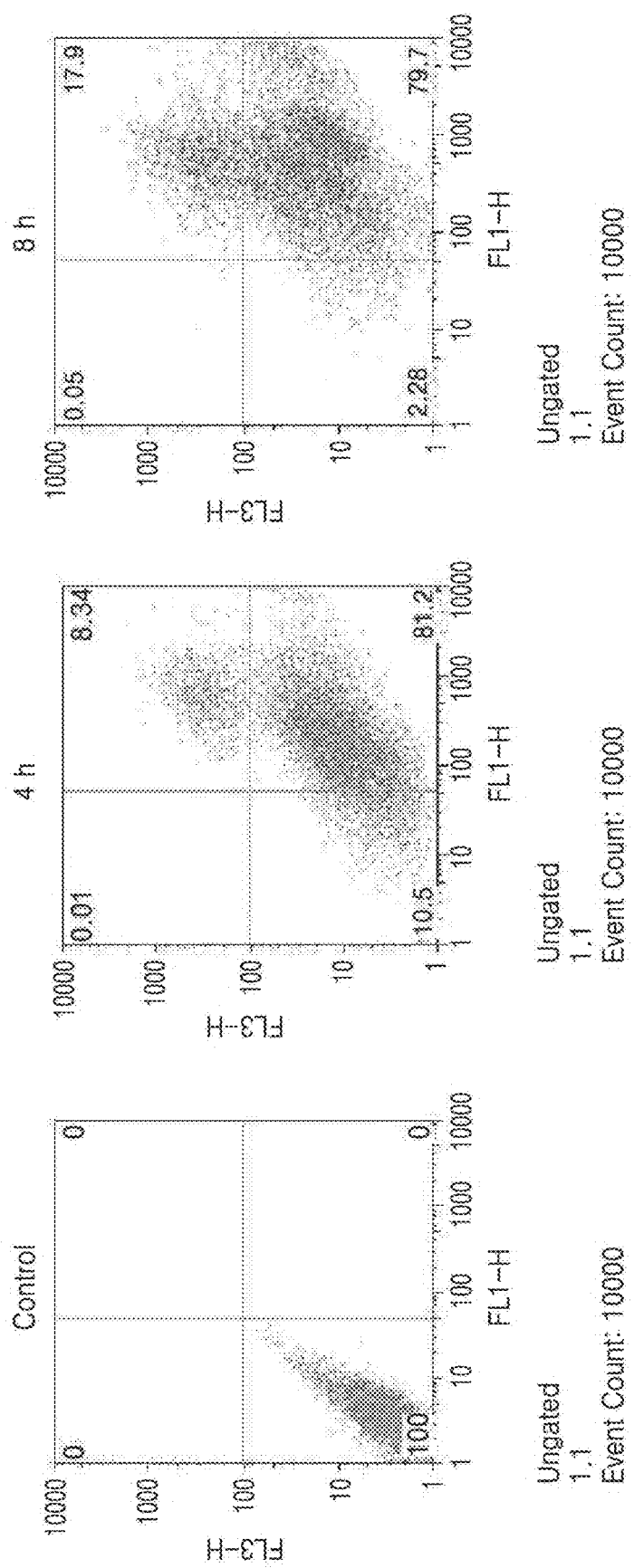
FIG. 35 shows that the early apoptosis caused by Mito-FF is confirmed by flow cytometric analysis, according to an embodiment.

As a result, as shown in FIG. 35, about 81.2% of the total population of the cells entered an early apoptotic stage within 2 hours, and a late apoptotic stage started after 10 hours.

Example 5. Cell Death Mechanism Induced by Mito-FF

Cell death induced by Mito-FF fibrils may arise from the synergism between two different mechanisms: (1) loss of mitochondrial membrane integrity and (2) promiscuous protein interactions.

Previous reports have shown that loss of integrity of endosomal/lysosomal membrane represents an early event in the pathogenesis of Aβ in Alzheimer's disease. Similarly, fibrous assembly of Mito-FF eventually was expected to result in the loss of mitochondrion membrane integrity. This expectation was proved by TEM analysis results.

A high positive charge possessed by the surface of Mito-FF fibers may promote their interaction with negatively charged membranes of mitochondria, which may consequently induce toxicity. To confirm this expectation, a liposomal leakage assay was conducted.

The release of a self-quenching dye such as calcine from liposome is commonly used to test integrity of lipid bilayers. Different concentrations of Mito-FF were used to test integrity of lipid bilayers. Different concentrations of Mito-FF were added to a vesicle-containing solution, and leakage of encapsulated calcein from the vesicle was monitored.

Figure 26:
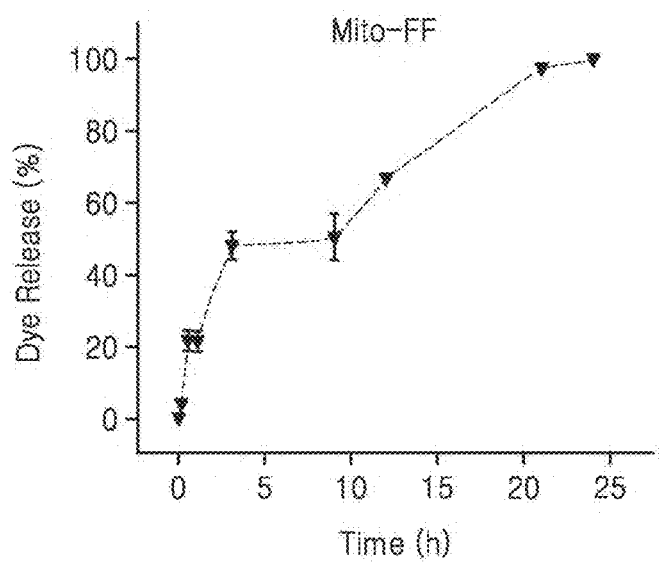
FIG. 26 is a graph of time vs. dye release, which shows model liposomal leakage induced by Mito-FF, according to an embodiment.

As shown in FIG. 26, the addition of Mito-FF caused the leakage of calcein in a time-dependent manner, and the leakage reached 100% within 24 hours. However at a concentration below the CAC, Mito-FF did not induce any dye leakage, which suggests that liposome leakage purely arises from interaction of fiber with liposome and not with molecules.

Figure 27:
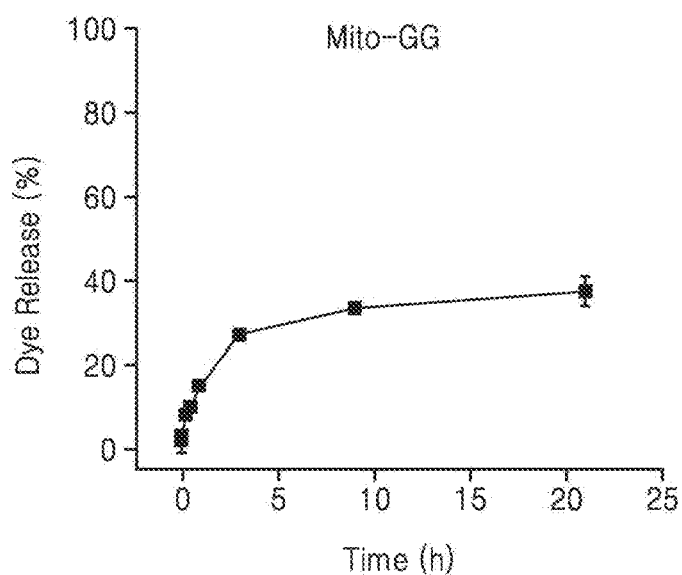
FIG. 27 is a graph of time vs. dye release, which shows model liposomal leakage induced by Mito-GG, according to an embodiment.

However, as shown in FIG. 27, Mito-GG, which forms micelles, induces only 30% of dye release within 24 hours, which suggests that micelles may not provide enough interaction with a mitochondrial membrane to cause decreased dysfunction of mitochondria induced by Mito-GG or spherical morphology.

To verify the mechanism that occurs after the membrane disruption with Mito-FF and Mito-GG, a molecular simulation was conducted using a Material Studio program available from Accelrys Inc., following the protocol of the manufacturer. The molecular simulation was performed between 2 μs and 1.56 μs, and the analysis thereof was converted to a final frame of 50 ns.

The simulation showed that Mito-FF fibers started forming a pore within 1.14 ns.

In an analysis of root mean square fluctuation (RMSF), the positions of particles were compared with reference positions over time, and the averaged fluctuated distance of each particle was shown. When Mito-FF interacted with plasma membrane, RMSF of penetration-inducing group may be larger than that of other groups.

The RMSF was measured by a molecular simulation using the Material Studio program available from Accelrys Inc. The molecular simulation was performed between 2 μs and 1.56 μs, and the analysis thereof was converted to a final frame of 50 ns.

Through the RMSF analysis, the interaction of Mito-FF with the plasma membrane was confirmed, and phenylalanine interacted most, followed by TPP.

On the basis of these results, it was found that the phenylalanine group of Mito-FF induced fiber formation, high surface density of TPP, and also the penetration through plasma membrane. Comparison of electrostatic and intermolecular potential energy between Mito-FF and plasma membrane may show which components contributed more towards the plasma membrane penetration. Electrostatic energy came from interaction of $P^+$ ions with plasma membrane, and intermolecular potential energy came from interaction of other groups except ions and plasma membrane. The electrostatic energy and intermolecular potential energy show an interval of penetration from 600 ns to 2000 ns. Electrostatic energy reached a stable state, but intermolecular potential energy decreased over time.

Figure 28:
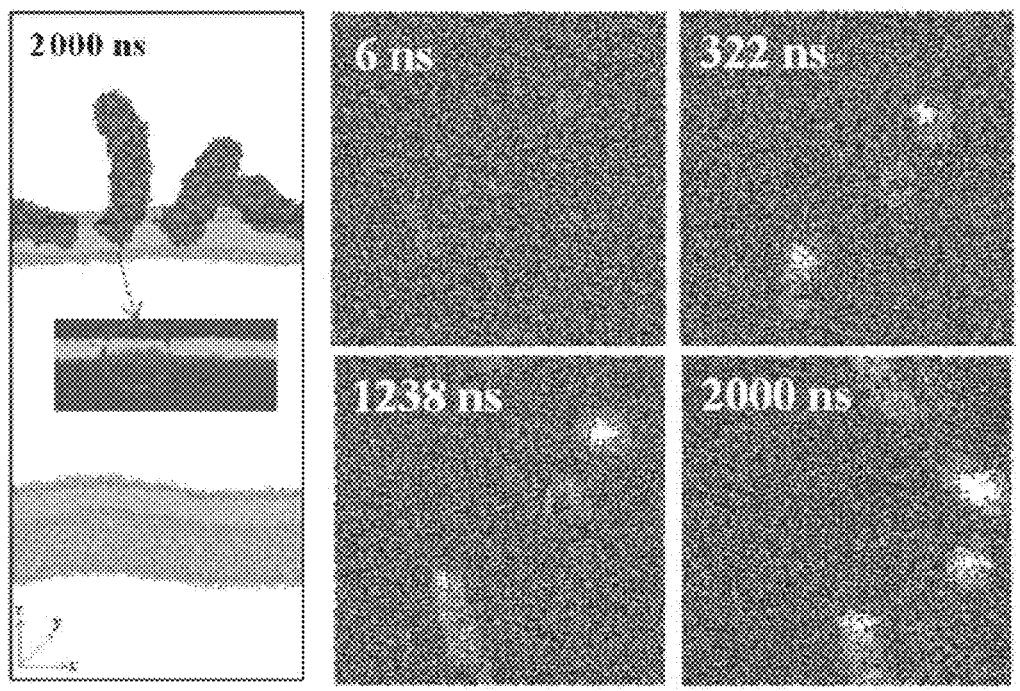
FIG. 28 shows the results of a molecular simulation and analysis of plasma membrane penetration ability of Mito-FF fibrils over time, according to an embodiment.

As shown in FIG. 28, during penetration, intermolecular potential energy maintained an unstable state, which suggests that TPP, phenyl, and pyrene groups, which include a benzene ring, interacted more than $P^+$ ions to penetrate the plasma membrane.

However, the Mito-GG which self-assembles to form a spherical structure, showed pyrene stacking, but not in the inner side of the sphere. Radial number density shows the structure of Mito-GG. Near a surface of the sphere, backbone groups had the highest density, followed by TPP and pyrene groups. Different from fiber structure, due to backbone groups surrounding the overall sphere, the surface density of benzene rings was lower than Mito-FF, which resulted in reduced membrane penetration of Mito-GG or spherical micelles.

As apparent from the foregoing description, a pharmaceutical composition for preventing or treating cancer may include a conjugate or a pharmaceutically acceptable salt thereof, wherein the conjugate may include a mitochondria-targeting moiety and a peptide represented by $(Xaa)_n$-Lys, the mitochondria-targeting moiety may be bound to the lysine (Lys), Xaa represents an amino acid, n indicates the number of Xaa bound via a peptide bond, n may be an integer from about 2 to about 200, Xaa may be selected from the group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine, tryptophan, and a variant bound to a $C_3$-$C_{10}$ cycloalkyl group, the amino acid may form a beta-sheet secondary structure between at least two amino acids, and the peptide may include the beta-sheet secondary structure. The pharmaceutical composition may be applicable to prevention or treatment of cancer.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A conjugate comprising: at least one mitochondria-targeting moiety and a peptide represented by $(Xaa)_n$-Lys, the mitochondria-targeting moiety being bound to a lysine (Lys) of the peptide, wherein Xaa represents an amino acid, n indicates the number of Xaa bound via a peptide bond, n is 2, Xaa is selected from the group consisting of valine, isoleucine, phenylalanine, cyclohexylalanine, threonine, cysteine, tyrosine, and tryptophan, wherein a beta-sheet secondary structure is formed between at least two amino acids, and the peptide is comprised in a beta sheet structure.

2. The conjugate of claim 1, wherein n is 2, and the amino acid is selected from the group consisting of phenylalanine, cyclohexylalanine, and valine.

3. The conjugate of claim 1, wherein a hydroxy group of a C-terminus carboxyl group of the lysine is substituted with a group selected from an amine group, an alkyl group, an alcohol group, a ketone group, an acyl group, an ester group, an ether group, an acetyl group, an acyl halide group, and an aldehyde group.

4. The conjugate of claim 1, wherein the number of the mitochondria-targeting moiety bound to the peptide is an integer from 1 to the number of amine groups present in the peptide represented by $(Xaa)_n$-Lys.

5. The conjugate of claim 1, wherein the mitochondria-targeting moiety is triphenylphosphonium (TPP).

6. The conjugate of claim 1, wherein the peptide is bound to the mitochondria-targeting moiety directly or via a linker.

7. The conjugate of claim 1, further comprising a fluorophore, the fluorophore being bound to the peptide.

8. The conjugate of claim 7, wherein the fluorophore is bound to an N-terminus of the peptide via an amide bond.

9. The conjugate of claim 7, wherein the fluorophore is selected from the group consisting of pyrene, 4-nitro-2,1,3-benzoxadiazole (NBD), perylene, naphthalene, and coronene.

10. The conjugate of claim 7, represented by Formula 2 or Formula 3:

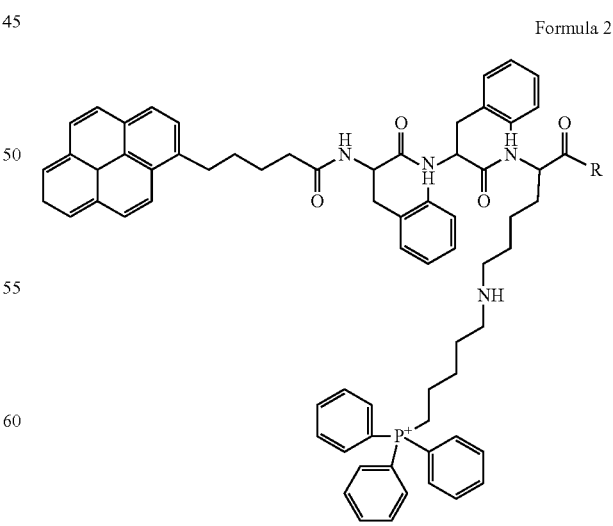

Formula 2

-continued

Formula 3

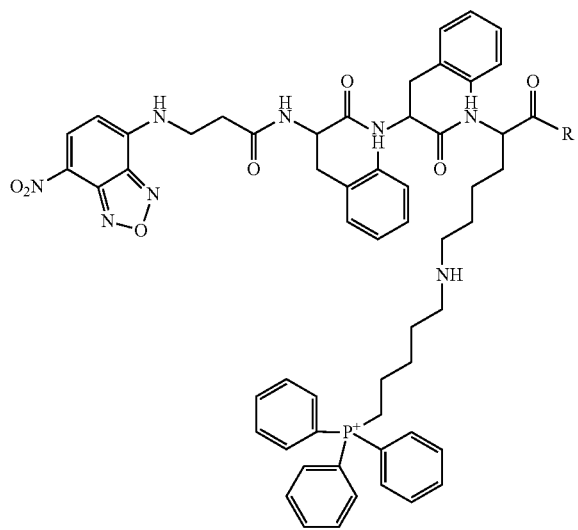

wherein R is the C-terminus of the peptide and is selected from at least one of the group consisting of a hydroxy group (—OH), an amine group, an alkyl group, an alcohol group, a ketone group, an acyl group, an ester group, an ether group, an acetyl group, an acyl halide group, and an aldehyde group, wherein the alkyl group, the alcohol group, the ketone group, the acyl group, the ester group, the ether group, the acetyl group, and the acyl halide group each independently have carbon atoms in a range of 1 to 20, 1 to 10, or 1 to 5.

11. A method of treating cancer, the method comprising: administering the conjugate of claim 1, or a pharmaceutically acceptable salt thereof, to a subject, wherein the amino acid is phenylalanine, cyclohexylalanine, or valine, and wherein the cancer is selected from cervical cancer, skin cancer, prostate cancer, mammary cancer, or breast cancer.

12. The method of claim 11, wherein the conjugate undergoes self-assembly in mitochondria of the cancer cells to induce apoptosis.

* * * * *